US010390890B2

(12) United States Patent
Jagga

(10) Patent No.: US 10,390,890 B2
(45) Date of Patent: Aug. 27, 2019

(54) NAVIGATIONAL FEEDBACK FOR INTRAOPERATIVE WAYPOINT

(71) Applicant: Arun Victor Jagga, Toronto (CA)

(72) Inventor: Arun Victor Jagga, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

(21) Appl. No.: 15/551,616

(22) PCT Filed: Jul. 27, 2015

(86) PCT No.: PCT/CA2015/050706
§ 371 (c)(1),
(2) Date: Aug. 17, 2017

(87) PCT Pub. No.: WO2017/015738
PCT Pub. Date: Feb. 2, 2017

(65) Prior Publication Data
US 2018/0042681 A1   Feb. 15, 2018

(51) Int. Cl.
| A61B 6/02 | (2006.01) |
| A61B 17/00 | (2006.01) |
| A61B 34/00 | (2016.01) |
| A61B 34/10 | (2016.01) |
| A61B 34/20 | (2016.01) |
| A61B 34/30 | (2016.01) |
| A61B 90/00 | (2016.01) |
| A61B 90/50 | (2016.01) |

(52) U.S. Cl.
CPC ............ *A61B 34/20* (2016.02); *A61B 6/02* (2013.01); *A61B 34/25* (2016.02); *A61B 34/70* (2016.02); *A61B 90/36* (2016.02); *A61B 90/361* (2016.02); *A61B 34/30* (2016.02); *A61B 2017/00115* (2013.01); *A61B 2034/107* (2016.02); *A61B 2034/2051* (2016.02); *A61B 2034/2055* (2016.02); *A61B 2034/2065* (2016.02); *A61B 2034/2068* (2016.02); *A61B 2090/365* (2016.02); *A61B 2090/502* (2016.02)

(58) Field of Classification Search
None
See application file for complete search history.

(56) References Cited

U.S. PATENT DOCUMENTS 6,741,883 B2 * 5/2004 Gildenberg ............ A61B 90/36
600/417
6,917,827 B2 * 7/2005 Kienzle, III ....... A61B 17/1703
600/427

(Continued)

*Primary Examiner* — Motilewa Good Johnson
(74) *Attorney, Agent, or Firm* — Ridout & Maybee LLP

(57) ABSTRACT

Methods and systems for providing navigational feedback during a surgical procedure. A user interface is displayed on a display for viewing position and orientation of a surgical tool in a surgical field during the surgical procedure. The position and orientation of the surgical tool is tracked by a medical navigation system coupled to the processor. The user interface includes a virtual representation of the surgical tool superimposed on an image of the surgical field. A selected intraoperative position and orientation of the surgical tool is used to intraoperatively create and store a waypoint in memory. Feedback is provided to indicate the stored position and orientation of the waypoint.

22 Claims, 16 Drawing Sheets

(56) References Cited

U.S. PATENT DOCUMENTS

| | | | |
|---|---|---|---|
| 7,605,826 B2* | 10/2009 | Sauer | G06F 3/04815 345/630 |
| 8,218,846 B2* | 7/2012 | Trumer | A61B 6/12 382/131 |
| 8,494,246 B2* | 7/2013 | Trumer | A61B 6/12 382/131 |
| 8,528,565 B2* | 9/2013 | Hauck | A61B 5/6885 128/898 |
| 9,129,359 B2* | 9/2015 | Averbuch | G06T 7/0012 |
| 9,639,666 B2* | 5/2017 | Baker | G06F 19/3437 |
| 9,788,714 B2* | 10/2017 | Krueger | A61B 3/0041 |
| 9,925,009 B2* | 3/2018 | Baker | A61B 34/10 |
| 2002/0140694 A1* | 10/2002 | Sauer | G06T 19/003 345/419 |
| 2002/0140709 A1* | 10/2002 | Sauer | G06F 3/011 345/633 |
| 2002/0163499 A1* | 11/2002 | Sauer | H04N 13/004 345/156 |
| 2003/0163040 A1* | 8/2003 | Gildenberg | A61B 90/36 600/429 |
| 2005/0148855 A1 | 7/2005 | Kienzle | |
| 2006/0058616 A1 | 3/2006 | Marquart et al. | |
| 2006/0063998 A1 | 3/2006 | Jako et al. | |
| 2007/0198008 A1* | 8/2007 | Hauck | A61B 5/6885 606/41 |
| 2010/0256558 A1* | 10/2010 | Olson | A61M 25/0147 604/95.01 |
| 2011/0015649 A1* | 1/2011 | Anvari | A61B 34/30 606/130 |
| 2013/0060146 A1* | 3/2013 | Yang | A61B 5/055 600/476 |
| 2013/0172906 A1* | 7/2013 | Olson | A61B 34/71 606/130 |
| 2014/0276033 A1* | 9/2014 | Brannan | A61B 6/03 600/431 |

* cited by examiner

NAVIGATIONAL FEEDBACK FOR INTRAOPERATIVE WAYPOINT

FIELD

The present disclosure relates to methods and systems for providing intraoperative navigational feedback. More particularly, the present disclosure relates to providing navigational feedback for navigating to an intraoperatively created waypoint.

BACKGROUND

While performing a surgical procedure with navigational assistance, a surgeon may wish to capture a current navigational view on the display screen that corresponds to a particular position of a tip of a pointer tool. This typically allows the surgeon to view the cross-sectional planes corresponding to the tool as well as the 3D view of the location of the tip. The captured view typically shows navigation information relating to the patient's anatomy, based on pre-operatively acquired images and the particular position of the pointer tool.

However, once the pointer tool is moved from the position at which the view was captured, it may be difficult or impossible for the surgeon to accurately and precisely return the tool to that particular position.

SUMMARY

In some example embodiments, the present disclosure provides a method, in a processor, for providing navigational feedback during a surgical procedure, the method may include: providing a user interface, displayed on a display coupled to the processor, for viewing position and orientation of a surgical tool in a surgical field during the surgical procedure, the position and orientation of the surgical tool being tracked by a medical navigation system coupled to the processor, the user interface including a virtual representation of the surgical tool superimposed on an image of the surgical field; intraoperatively creating a waypoint and storing, in a memory coupled to the processor, a selected intraoperative position and orientation of the surgical tool as stored position and orientation of the waypoint; and providing feedback to indicate the stored position and orientation of the waypoint.

In some example embodiments, the present disclosure provides a system for providing navigational feedback during a surgical procedure, the system may include: a display for displaying a user interface, the user interface comprising a display of a virtual representation of a tracked position and orientation of a surgical tool superimposed on an image of a surgical field, the position and orientation of the surgical tool being tracked by a medical navigation system during the surgical procedure; and a processor coupled to the medical navigation system and the display, the processor being configured to execute instructions to cause the system to: intraoperatively create a waypoint and store, in a memory coupled to the processor, a selected intraoperative position and orientation of the surgical tool as stored position and orientation of the waypoint; and display feedback on the user interface to indicate the stored position and orientation of the waypoint, the feedback being displayed superimposed on the image of the surgical field.

In some examples, the system may include the medical navigation system configured to track position and orientation of the surgical tool in the surgical field during the surgical procedure.

In some example embodiments, the present disclosure provides computer readable products for providing navigational feedback during a surgical procedure, the computer readable product comprising computer-executable instructions that, when executed, causes a computer system to carry out the method as described above.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DESCRIPTION OF EXAMPLE EMBODIMENTS

The systems and methods described herein may be useful in the field of surgery. The present disclosure provides examples in the field of neurosurgery, such as for oncological care, treatment of neurodegenerative disease, stroke, and brain trauma. Persons of skill will appreciate the ability to extend these concepts to other conditions or fields of medicine. It should be noted that while the present disclosure describes examples in the context of neurosurgery, the present disclosure may be applicable to other procedures that may benefit from intraoperative navigational feedback with respect to an intraoperatively created waypoint. For example, the present disclosure may also be applicable to the field of spinal surgery or orthopedic surgery, among others.

Various example apparatuses or processes will be described below. No example embodiment described below limits any claimed embodiment and any claimed embodiments may cover processes or apparatuses that differ from those examples described below. The claimed embodiments are not limited to apparatuses or processes having all of the features of any one apparatus or process described below or to features common to multiple or all of the apparatuses or processes described below. It is possible that an apparatus or process described below is not an embodiment of any claimed embodiment.

Furthermore, numerous specific details are set forth in order to provide a thorough understanding of the disclosure. However, it will be understood by those of ordinary skill in the art that the embodiments described herein may be practiced without these specific details. In other instances, well-known methods, procedures and components have not been described in detail so as not to obscure the embodiments described herein.

Figure 1:
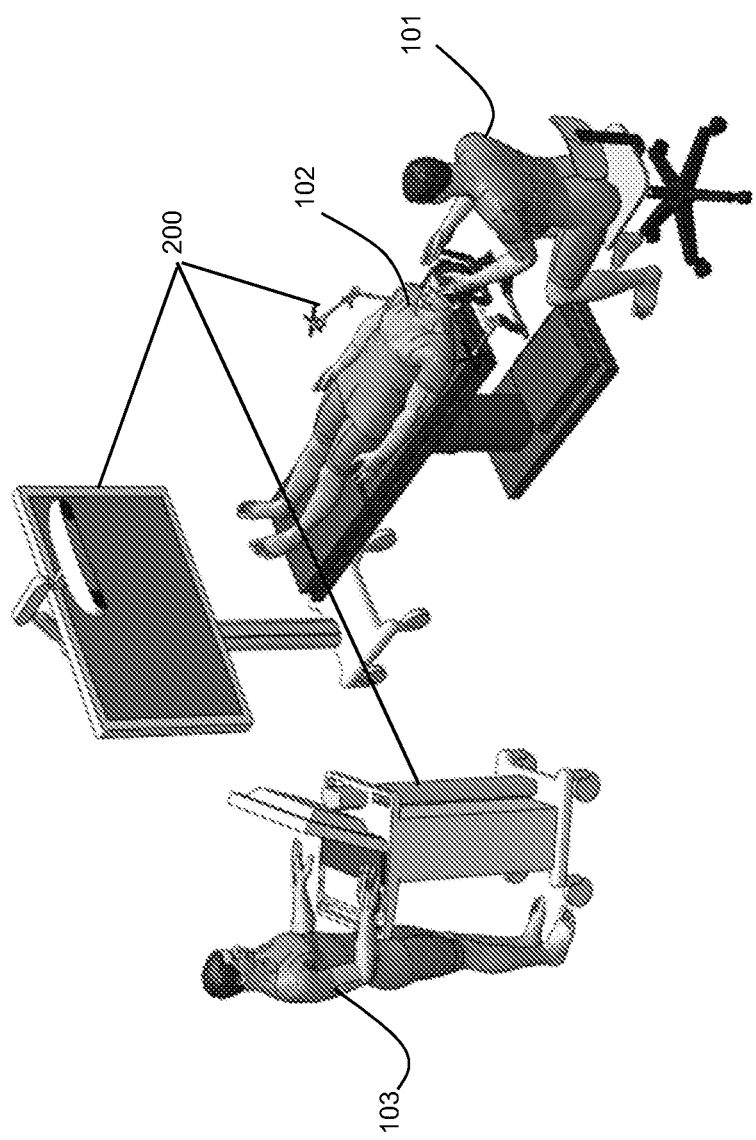
FIG. 1 shows an example minimally invasive port-based surgical procedure.

FIG. 1 illustrates a perspective view of an example minimally invasive port-based surgical procedure. As shown in FIG. 1, a surgeon 101 may conduct a minimally invasive port-based surgery on a patient 102 in an operating room (OR) environment. A craniotomy may be performed as part of the minimally invasive surgery, to provide access to the patient's brain. A localization or navigation system 200 (described further below) may be used to assist the surgeon 101 during the procedure. Optionally, an operator 103 may be present to operate, control and provide assistance with the navigation system 200.

Figure 2:
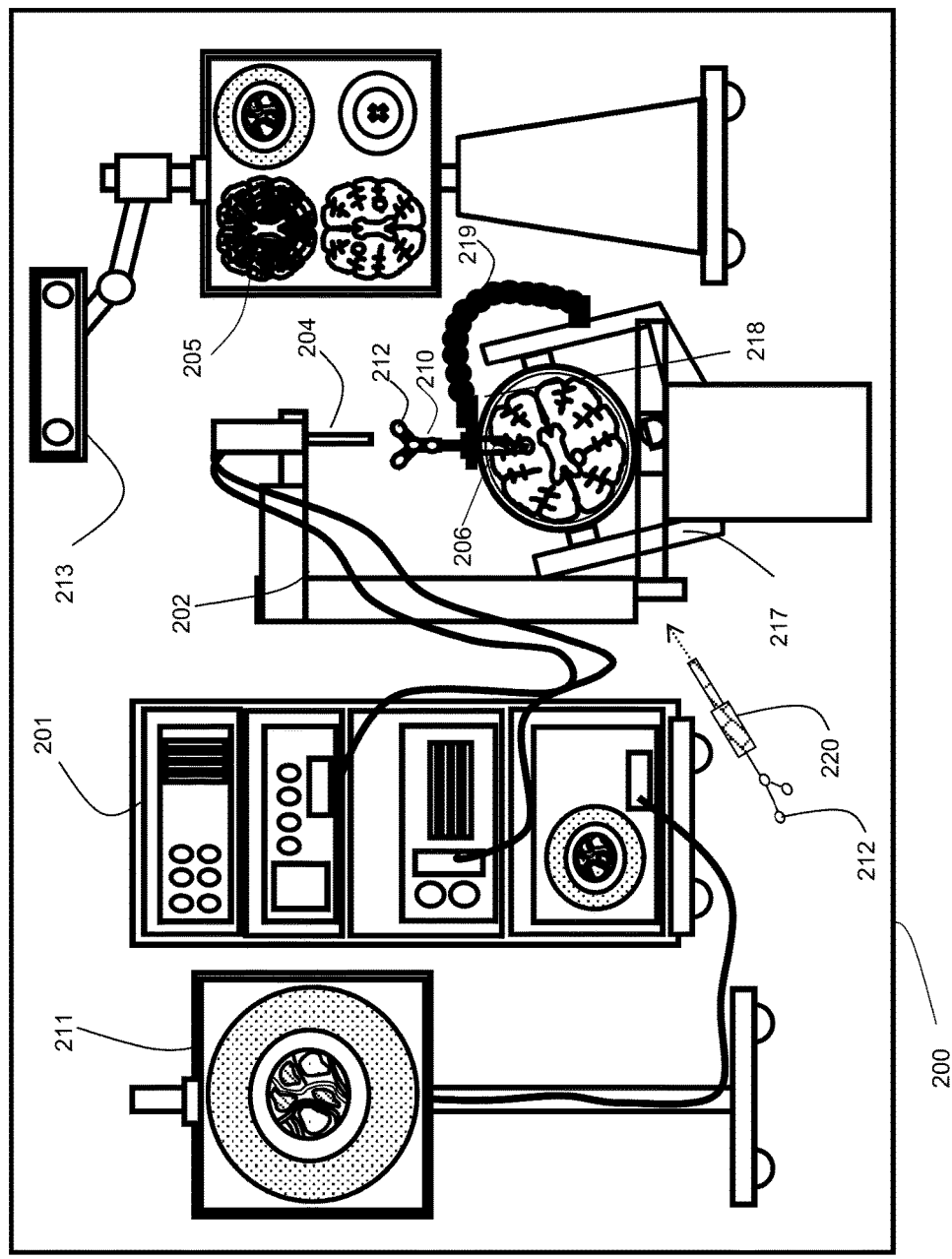
FIG. 2 is a diagram illustrating system components of an example navigation system.

FIG. 2 shows a diagram illustrating components of an example medical navigation system 200. The disclosed methods and systems for providing navigational feedback may be implemented in the context of the medical navigation system 200. The medical navigation system 200 may include one or more displays 205, 211 for displaying still and/or video images (e.g., a live video image of the surgical field and/or 2D or 3D images obtained preoperatively), an equipment tower 201, and a mechanical arm 202, which may support an optical scope 204 (which may also be referred to as an external scope). One or more of the displays 205, 211 may include a touch-sensitive display for receiving touch input. The equipment tower 201 may be mounted on a frame (e.g., a rack or cart) and may contain a power supply and a computer or controller that may execute planning software, navigation software and/or other software to manage the mechanical arm 202 and tracked instruments. In some examples, the equipment tower 201 may be a single tower configuration operating with multiple displays 211, 205, however other configurations may also exist (e.g., multiple towers, single display, etc.). Furthermore, the equipment tower 201 may also be configured with a universal power supply (UPS) to provide for emergency power, in addition to a regular AC adapter power supply.

A portion of the patient's anatomy may be held in place by a holder. For example, in the context of a neurosurgical procedure, the patient's head and brain may be held in place by a head holder 217. An access port 206 and associated introducer 210 may be inserted into the head, to provide access to a surgical site in the head. The optical scope 204 may be attached to the mechanical arm 202, and may be used to view down the access port 206 at a sufficient magnification to allow for enhanced visibility down the access port 206. The output of the optical scope 204 may be received by one or more computers or controllers to generate a view that may be depicted on a visual display (e.g., one or more displays 205, 211).

In some examples, the navigation system 200 may include a tracked surgical tool 220, which may include markers 212 to enable tracking by a tracking camera 213. An example of a tracked surgical tool 220 may be a pointer tool, which may be used to identify points (e.g., fiducial points or points bordering a craniotomy opening, as discussed below) on a patient. For example, an operator, typically a nurse or the surgeon 101, may use the pointer tool to identify the location of points on the patient 102, in order to register the location of selected points on the patient 102 in the navigation system 200. It should be noted that a guided robotic system with closed loop control may be used as a proxy for human interaction. Guidance to the robotic system may be provided by any combination of input sources such as image analysis, tracking of objects in the operating room using markers placed on various objects of interest, or any other suitable robotic system guidance techniques.

Fiducial markers 212 may also be connected to the introducer 210 for tracking by the tracking camera 213, which may provide positional information of the introducer 210 from the navigation system 200. In some examples, the fiducial markers 212 may be alternatively or additionally attached to the access port 206. Other surgical tools (not shown) may be provided with markers 212 to enable tracking by the tracking camera 213. In some examples, the tracking camera 213 may be a 3D infrared optical tracking stereo camera similar to one made by Northern Digital Imaging (NDI). In some examples, the tracking system 213 may be an electromagnetic system (not shown), such as a field transmitter that may use one or more receiver coils located on the tool(s) to be tracked. Known profile of the electromagnetic field and known position of receiver coil(s) relative to each other may be used to infer the location of the tracked tool(s) using the induced signals and their phases in each of the receiver coils. Operation and examples of this technology is further explained in Chapter 2 of "Image-Guided Interventions Technology and Application," Peters, T.; Cleary, K., 2008, ISBN: 978-0-387-72856-7, incorporated herein by reference. Location data of the mechanical arm 202 and/or access port 206 may be determined by the tracking camera 213 by detection of the fiducial markers 212 placed on or otherwise in fixed relation (e.g., in rigid connection) to any of the mechanical arm 202, the access port 206, the introducer 210, the tracked surgical tool 220 and/or other tools. The fiducial marker(s) 212 may be active or passive markers. The display 205, 211 may provide output of the computed data of the navigation system 200. In some examples, the output provided by the display 205, 211 may include axial, sagittal and coronal views of patient anatomy as part of a multi-view output.

The active or passive fiducial markers 212 may be placed on tool(s) (e.g., the access port 206 and/or the optical scope 204) to be tracked, to determine the location and orientation of these tool(s) using the tracking camera 213 and navigation system 200. The markers 212 may be captured by the tracking camera 213 (which may be a stereo camera) to give identifiable points for tracking the tool(s). A tracked tool may be defined by a grouping of markers 212, which may define a rigid body to the tracking system. This may in turn be used to determine the position and/or orientation in 3D of a tracked tool in a virtual space. The position and orientation of the tracked tool in 3D may be tracked in six degrees of freedom (e.g., x, y, z coordinates and pitch, yaw, roll rotations), in five degrees of freedom (e.g., x, y, z, coordinate and two degrees of free rotation), but preferably tracked in at least three degrees of freedom (e.g., tracking the position of the tip of a tool in at least x, y, z coordinates). In typical use with navigation systems, at least three markers 212 are provided on a tracked tool to define the tool in virtual space, however it is known to be advantageous for four or more markers 212 to be used.

Camera images capturing the markers 212 may be logged and tracked, by, for example, a closed circuit television (CCTV) camera. The markers 212 may be selected to enable or assist in segmentation in the captured images. For example, infrared (IR)-reflecting markers and an IR light source from the direction of the camera may be used. An example of such an apparatus may be tracking devices such as the Polaris® system available from Northern Digital Inc. In some examples, the spatial position of the tracked tool and/or the actual and desired position of the mechanical arm 202 may be determined by optical detection using a camera. The optical detection may be done using an optical camera, rendering the markers 212 optically visible.

In some examples, the markers 212 (e.g., reflectospheres) may be used in combination with a suitable tracking system, to determine the spatial positioning position of the tracked tools within the operating theatre. Different tools and/or targets may be provided with respect to sets of markers 212 in different configurations. Differentiation of the different tools and/or targets and their corresponding virtual volumes may be possible based on the specification configuration and/or orientation of the different sets of markers 212 relative to one another, enabling each such tool and/or target to have a distinct individual identity within the navigation system 200. The individual identifiers may provide information to the system, such as information relating to the size and/or shape of the tool within the system. The identifier may also provide additional information such as the tool's central point or the tool's central axis, among other information. The virtual tool may also be determinable from a database of tools stored in or provided to the navigation system 200. The markers 212 may be tracked relative to a reference point or reference object in the operating room, such as the patient 102.

Various types of markers may be used. The markers 212 may all be the same type or may include a combination of two or more different types. Possible types of markers that could be used may include reflective markers, radiofrequency (RF) markers, electromagnetic (EM) markers, pulsed or un-pulsed light-emitting diode (LED) markers, glass markers, reflective adhesives, or reflective unique structures or patterns, among others. RF and EM markers may have specific signatures for the specific tools they may be attached to. Reflective adhesives, structures and patterns, glass markers, and LED markers may be detectable using optical detectors, while RF and EM markers may be detectable using antennas. Different marker types may be selected to suit different operating conditions. For example, using EM and RF markers may enable tracking of tools without requiring a line-of-sight from a tracking camera to the markers 212, and using an optical tracking system may avoid additional noise from electrical emission and detection systems.

In some examples, the markers 212 may include printed or 3D designs that may be used for detection by an auxiliary camera, such as a wide-field camera (not shown) and/or the optical scope 204. Printed markers may also be used as a calibration pattern, for example to provide distance information (e.g., 3D distance information) to an optical detector. Printed identification markers may include designs such as concentric circles with different ring spacing and/or different types of bar codes, among other designs. In some examples, in addition to or in place of using markers 212, the contours of known objects (e.g., the side of the access port 206) could be captured by and identified using optical imaging devices and the tracking system.

Minimally invasive brain surgery using an access port 206 is a method of performing surgery on brain tumors. In order to introduce an access port 206 into the brain, the introducer 210, having an atraumatic tip, may be positioned within the access port 206 and employed to position the access port 206 within the patient's brain. The introducer 210 may include fiducial markers 212 for tracking position and orientation of the introducer 210. The fiducial markers 212 may be passive (e.g., reflective spheres for use with an optical tracking system, or pick-up coils for use with an electromagnetic tracking system). The fiducial markers 212 may be detected by the tracking camera 213 and the respective positions of the tracked tool may be inferred by tracking software executed by a computer or controller in connection with the navigation system 200.

Once the access port 206 has been positioned into the brain, the associated introducer 210 may be removed to allow for access to the surgical site of interest, through the central opening of the access port 206. Tracking of the access port 206 may be provided by an access port guide or by attaching markers to the access port 206 itself.

A guide clamp 218 (or more generally a guide) for holding the access port 206 may be provided. The guide clamp 218 may allow the access port 206 to be held at a fixed position and orientation while freeing up the surgeon's hands. An articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g., on another patient support, such as on the surgical bed), to ensure that when locked in place, the guide clamp 218 does not move relative to the patient's head.

In a surgical operating room (or theatre), setup of a navigation system may be relatively complicated; there may be many pieces of equipment associated with the surgical procedure, as well as elements of the navigation system 200. Further, setup time typically increases as more equipment is added. To assist in addressing this, the navigation system 200 may include two additional wide-field cameras to enable video overlay information. One wide-field camera may be mounted on the optical scope 204, and a second wide-field camera may be mounted on the tracking camera 213. Video overlay information can then be inserted into displayed images, such as images displayed on one or more of the displays 205, 211. The overlay information may illustrate the physical space where accuracy of the 3D tracking system (which is typically part of the navigation system) is greater, may illustrate the available range of motion of the mechanical arm 202 and/or the optical scope 204, and/or may help to guide head and/or patient positioning.

The navigation system 200 may provide tools to the neurosurgeon that may help to provide more relevant information to the surgeon, and may assist in improving performance and accuracy of port-based neurosurgical operations. Although described in the present disclosure in the context of port-based neurosurgery (e.g., for removal of brain tumors and/or for treatment of intracranial hemorrhages (ICH)), the navigation system 200 may also be suitable for one or more of: brain biopsy, functional/deep-brain stimulation, catheter/shunt placement (in the brain or elsewhere), open craniotomies, and/or endonasal/skull-based/ear-nose-throat (ENT) procedures, as well as surgical procedures other than neurosurgical procedures. The same navigation system 200 may be used for carrying out any or all of these procedures, with or without modification as appropriate.

For example, although the present disclosure may discuss the navigation system 200 in the context of neurosurgery, the same navigation system 200 may be used to carry out a diagnostic procedure, such as brain biopsy. A brain biopsy may involve the insertion of a thin needle into a patient's brain for purposes of removing a sample of brain tissue. The brain tissue may be subsequently assessed by a pathologist to determine if it is cancerous, for example. Brain biopsy procedures may be conducted with or without a stereotactic frame. Both types of procedures may be performed using image-guidance. Frameless biopsies, in particular, may be conducted using the navigation system 200.

In some examples, the tracking camera 213 may be part of any suitable tracking system. In some examples, the tracking camera 213 (and any associated tracking system that uses the tracking camera 213) may be replaced with any suitable tracking system which may or may not use camera-based tracking techniques. For example, a tracking system that does not use the tracking camera 213, such as a radiofrequency tracking system, may be used with the navigation system 200.

Figure 16:
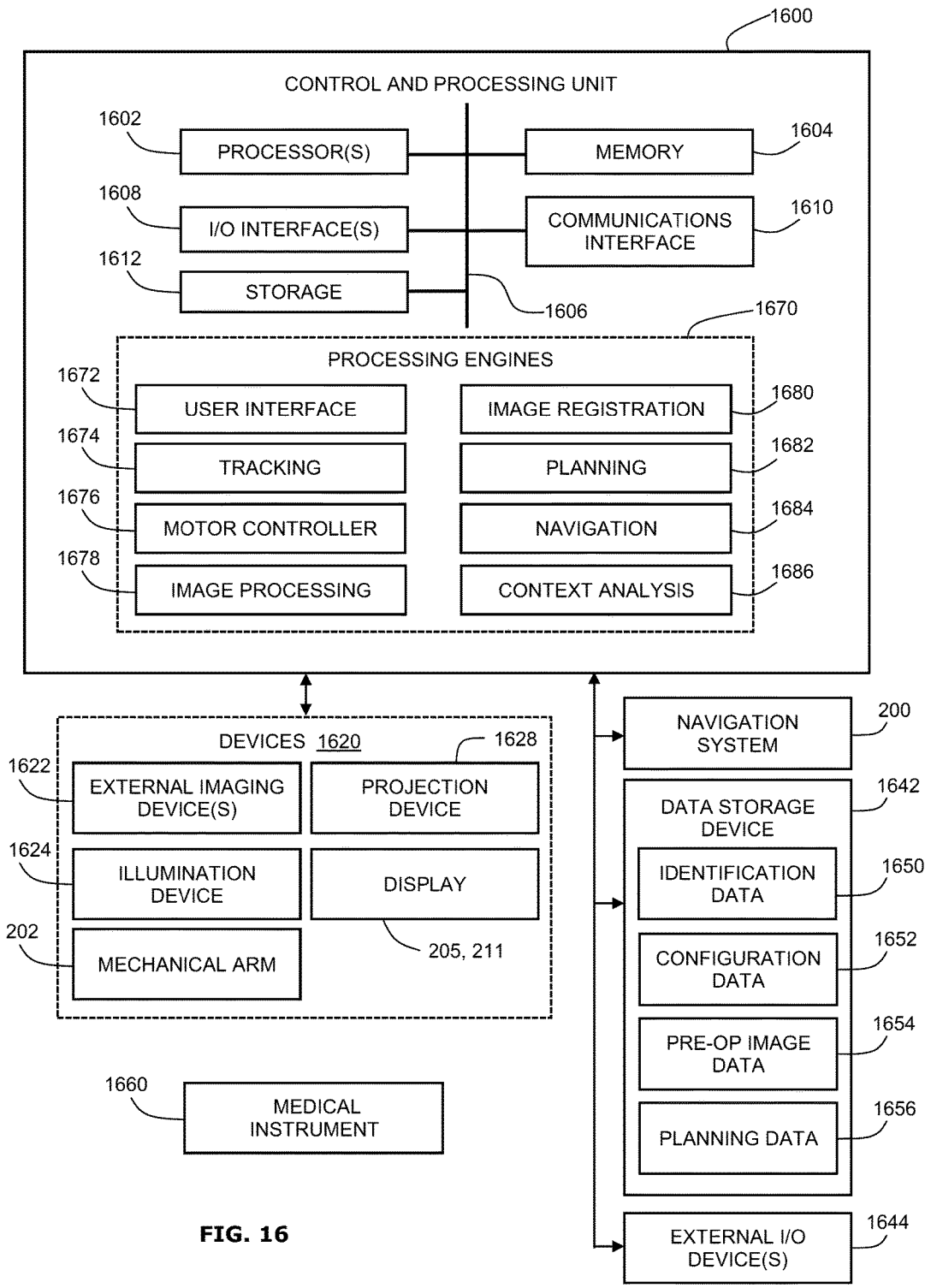
FIG. 16 is a flowchart illustrating an example method for providing navigational feedback during a surgical procedure.

FIG. 16 shows a block diagram of an example system configuration that may be used to carry out the functions of a navigation system, as disclosed herein. The example system may include a control and processing unit 1600 and other external components.

In some examples, the control and processing unit 1600 may include one or more processors 1602 (for example, a CPU and/or microprocessor), one or more memories 1604 (which may include random access memory (RAM) and/or read-only memory (ROM)), a system bus 1606, one or more input/output interfaces 1608 (such as a user interface for a user (e.g., a clinician or a surgeon) to provide various inputs (e.g., to perform trajectory planning or run simulations)), one or more communications interfaces 1610, and one or more internal storage devices 1612 (e.g. a hard disk drive, compact disk drive and/or internal flash memory). The control and processing unit may also include a power supply (not shown).

The control and processing unit 1600 may interface with one or more other external devices, such as a tracking system or navigation system (e.g., the navigation system 200 of FIG. 2), a data storage device 1642, and external input and/or output devices 1644 which may include, for example, one or more of a display, keyboard, mouse, foot pedal, microphone and speaker. The data storage device 1642 may include any one or more suitable data storage devices, such as a local or remote computing device (e.g., a computer, a hard drive, a digital media device, or a server) which may have a database stored thereon. In the example shown in FIG. 16, the data storage device 1642 may store identification data 1650 for identifying one or more medical instruments 1660 and configuration data 1652 that may associate customized configuration parameters with the one or more medical instruments 1660. The data storage device 1642 may also store preoperative image data 1654 and/or medical procedure planning data 1656. Although the data storage device 1642 is shown as a single device, the data storage device 1642 may be provided as one or more storage devices.

The medical instrument(s) 1660 may be identifiable by the control and processing unit 1600. The medical instrument(s) 1660 may be connected to, and controlled by, the control and processing unit 1600, or may be operated or otherwise employed independently of the control and processing unit 1600. The navigation system 200 may be employed to track one or more of the medical instrument(s) 1660 and spatially register the one or more tracked medical instruments 1660 to an intraoperative reference frame.

The control and processing unit 1600 may also interface with one or more other configurable devices 1620, and may intraoperatively reconfigure one or more of such device(s) 1620 based on configuration parameters obtained from configuration data 1652, for example. Examples of the device(s) 1620 may include one or more external imaging devices 1622, one or more illumination devices 1624, the mechanical arm 202, one or more projection devices 1628, and one or more displays 205, 211.

Various embodiments and aspects of the present disclosure may be implemented via the processor(s) 1602 and/or memory(ies) 1604. For example, one or more of the functionalities and methods described herein may be at least partially implemented via hardware logic in the processor(s) 1602 and/or at least partially using instructions stored in the memory(ies) 1604, as one or more processing engines 1670 (also referred to as modules). Example processing engines 1670 include, but are not limited to, a user interface engine 1672, a tracking engine 1674, a motor controller 1676, an image processing engine 1678, an image registration engine 1680, a procedure planning engine 1682, a navigation engine 1684, and a context analysis engine 1686. Although certain engines (or modules) are described, it should be understood that engines or modules need not be specifically defined in the instructions, and an engine or module may be used to implement any combination of functions.

It is to be understood that the system is not intended to be limited to the components shown in FIG. 16. For example, one or more components of the control and processing unit 1600 may be provided as an external component or device. Although only one of each component is illustrated in FIG. 16, any number of each component can be included. For example, a computer typically contains a number of different data storage media. Furthermore, although the bus 1606 is depicted as a single connection between all of the components, the bus 1606 may represent one or more circuits, devices or communication channels which link two or more of the components. For example, in personal computers, the bus 1606 may include or may be a motherboard.

In some examples, the navigation engine 1684 may be provided as an external navigation system that may interface with or be integrated with the control and processing unit 1600.

Some embodiments or aspects of the present disclosure may be implemented using the processor 1602 without additional instructions stored in the memory 1604. Some embodiments or aspects of the present disclosure may be implemented using instructions stored in the memory 1604 for execution by one or more general purpose microprocessors. In some examples, the control and processing unit 1600 (which may be also referred to as a computer control system) may be, or may include, a general purpose computer or any other hardware equivalents configured for operation in space. The control and processing unit 1600 may also be implemented as one or more physical devices that may be coupled to the processor(s) 1602 through one or more communications channels or interfaces. Far example, the control and processing unit 1600 may be implemented using application specific integrated circuits (ASIC). In some examples, the control and processing unit 1600 may be implemented as a combination of hardware and software, such as where the software may be loaded into the processor(s) 1602 from the memory(ies) 1604 or internal storage(s) 1612, or from an external source (e.g., via the communication interface(s) 1610, such as over a network connection). Thus, the present disclosure is not limited to a specific configuration of hardware and/or software.

Figure 3:
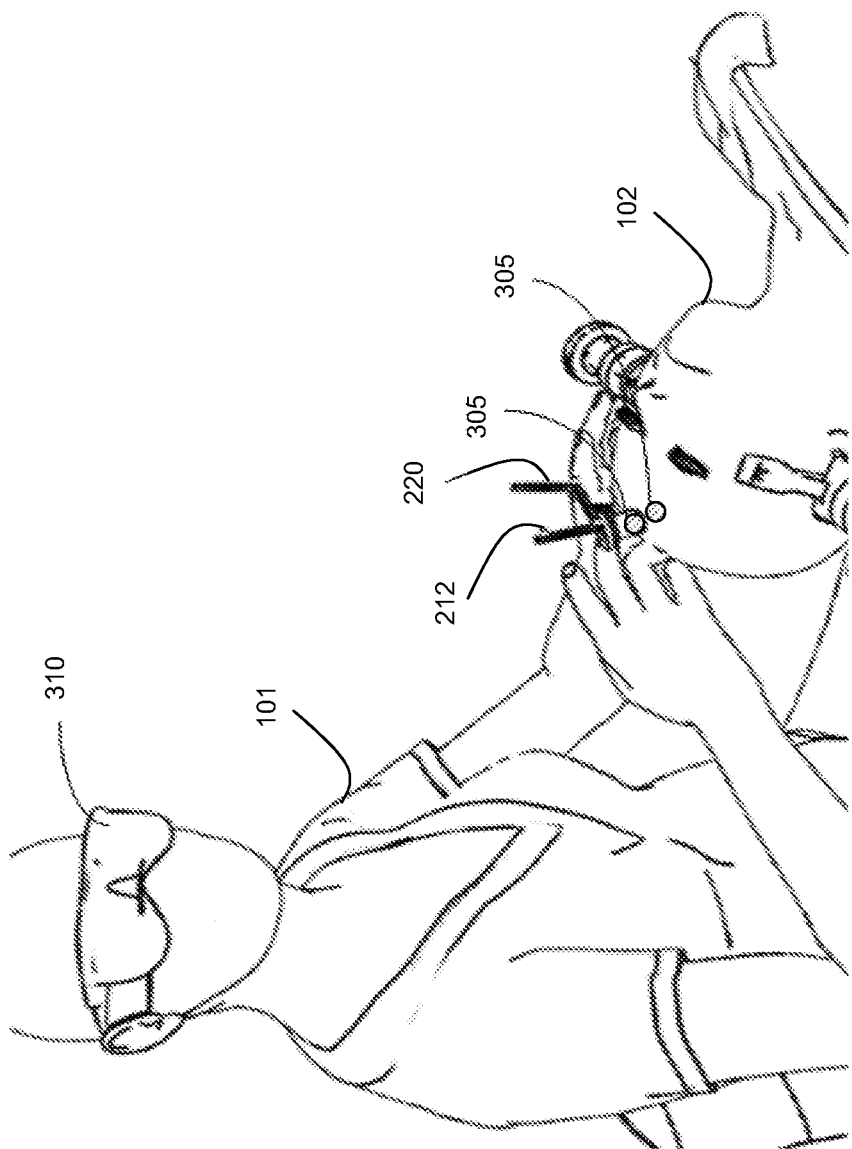
FIG. 3 is a diagram illustrating an example neurosurgical procedure in which waypoints have been intraoperatively defined.

FIG. 3 illustrates an example neurosurgical procedure in which the surgeon 101 has intraoperatively defined a plurality of waypoints 305, in accordance with an example of the present disclosure. In the present disclosure, the term "waypoint" may be used to refer to a defined point at a specified location and possibly a specified orientation. Such a waypoint 305 may be used as a reference point, a "landmark", a guide point or a "home" point, for example. The waypoint may provide navigational feedback by serving as a home point to which the surgical tool should return to, by serving as a reference point or landmark (e.g., giving the surgeon a sense of direction and relative distance) and/or by providing information about direction and/or distance to another point of interest, for example. Other features and functions of the waypoint will be apparent in the present description.

In this example, the surgeon 101 has introduced the surgical tool 220, having fiducial markers 212, into the skull of the patient 102. The surgical tool 220 may be tracked by the navigation system 200, as described above. The surgeon 101 may define one or more waypoints 305 in the virtual space. The surgeon 101 may be able to view the waypoints 305 in the virtual space and/or virtually superimposed on the actual surgical site using augmented reality glasses 310, for example.

Other techniques for providing feedback to the surgeon 101 about the position and orientation of the waypoints 305 may be used, as discussed further below. In the example of FIG. 3, two waypoints 305 are shown as shaded circles. It should be understood that the waypoint(s) 305 may be represented in other ways, and may not be intended to be viewable on the actual patient 102. The waypoint(s) 305 may be created intraoperatively using a user interface (e.g., a user interface provided by the navigation system 200 and displayed on a display 205, 211), as discussed further below.

Figure 4:
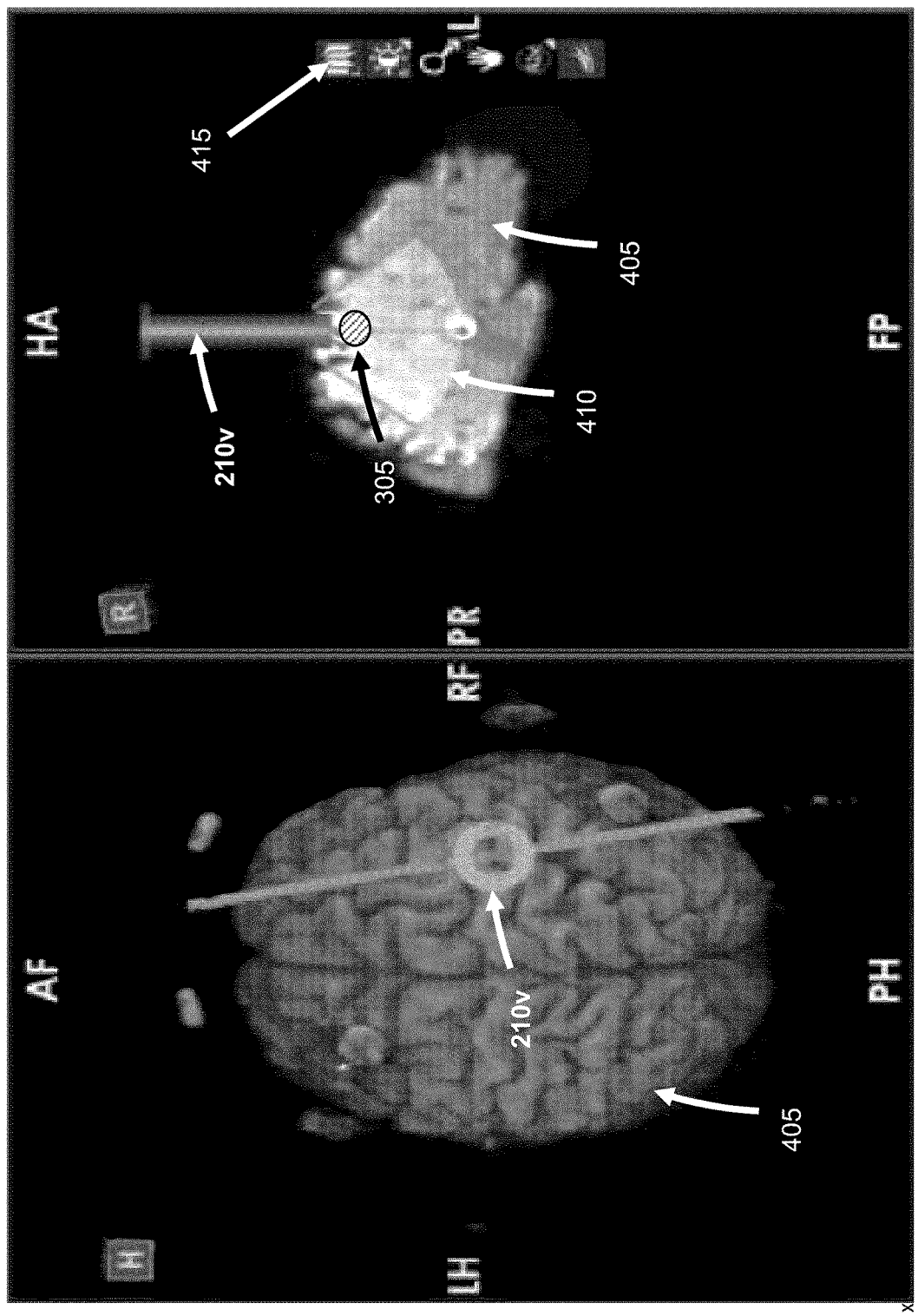
FIG. 4 shows an example user interface that may be displayed intraoperatively to provide navigational feedback.

FIG. 4 shows an example user interface that may be displayed intraoperatively to provide navigational feedback. The user interface includes on the left a perspective view of the surgical field including a 3D image 405 of the patient's brain; and on the right cross-sectional view of the 3D image 405. In both views, a virtual representation 210v of the access port 210 is shown, corresponding to the actual position and location of the access port 210 in the surgical field. The right-side cross-sectional view is along the plane defined by the access port 210, which plane is depicted as a line passing through the virtual representation 210v on the left-side view. In some examples, more or less views may be provided, which may be different from those shown in FIG. 4. For example, the user interface may include a live video image of the procedure (e.g., as captured by an endoscope) with virtual representations superimposed thereon.

Generally, the image of the surgical field provided by the user interface may include a real-time view, such as a real-time view of the actual surgical field (e.g., as captured by an endoscope or an exoscope), a real-time view of a virtual surgical field (e.g., a virtual view that tracks the procedure in real-time), a real-time view of a preoperative image (e.g., a view of the preoperative image that tracks the procedure in real-time), or a combination thereof. The image of the surgical field provided by the user interface may additionally or alternatively include a static or non-real-time view, such as a static preoperative image or static 3D model of the surgical field.

The right-side view also includes a highlighted area 410 representing the available range of motion of the access port 210, and a representation of a virtual waypoint 305. The waypoint 305 may be created intraoperatively using user interface tools provided by the user interface, for example using a toolbar 415 presented in the user interface. Unlike navigational guides that are created pre-operatively during the planning stage, a waypoint 305 is a navigational guide that may be created intraoperatively. Thus, initially, there is no waypoint until the surgeon 101 creates one during the procedure.

An example of how a waypoint 305 may be created will now be described. As the surgeon 101 advances a tool 220 (e.g., the access port 210 or other surgical tool 220) during the procedure, the position and orientation of the tool 220 may be tracked by the navigation system 200. The user interface may be updated to reflect the current position and orientation of the surgical tool 220, for example superimposed on pre-operative images of the surgical target (e.g., 3D images such as magnetic resonance (MR) or computed tomography (CT) images). Where the user interface includes a display of cross-sectional view(s), the location and orientation of the cross-section(s) may change to correspond to the current position and orientation of the surgical tool 220 as it is being moved.

At any point during the procedure, the surgeon 101 may wish to capture or freeze the current view(s) in the user interface. This may be done through the selection of a button provided by a toolbar 415 in the user interface, for example using a foot pedal or other input device. The captured view(s) thus correspond to a selected position and orientation of the surgical tool 220. The capture view(s) may be stored (e.g., in a memory associated with the user interface or the navigation system 200). A waypoint 305 may be created automatically when the view(s) are captured or in response to further input (e.g., further selection of a button on the toolbar 415). The waypoint 305 may thus be created intraoperatively to store (e.g., in a memory associated with the user interface or the navigation system 200) the position and orientation of the surgical tool 220 at the position and orientation at which the captured view(s) are captured. In some examples, the waypoint 305 may be stored in association with the stored captured view(s). In some examples, only the waypoint 305 may be stored but not the captured view(s); instead, the captured view(s) may be regenerated for later viewing, from pre-operative images, using the stored position and orientation information of the waypoint 305

After viewing the captured view(s) (or optionally without viewing the captured view(s)), the surgeon 101 may continue the procedure and move the surgical tool 220. After the surgical tool 220 has been moved, feedback (e.g., visual, audio and/or tactile feedback) may be provided to the surgeon to indicate the stored position and orientation of the waypoint 305 (e.g., to guide return of the surgical tool 220 to the waypoint 305 and/or to serve as a reference point). In some examples, such feedback may be provided automatically (e.g., in the form of a persistent visual representation of the waypoint 305, such as in FIG. 4) as soon as the waypoint 305 is created. In some examples, such feedback may be provided only in response to user input (e.g., selection of a button on the toolbar 415).

In some examples, the waypoint 305 may be created intraoperatively without the surgeon 101 providing input to capture a view. For example, the surgeon 101 may wish to create a waypoint 305 (e.g., as a point of reference) without necessarily being interested in capturing the view. In such situations, the waypoint 305 may be created, similarly to the above description, in response to input (e.g., selection of a button on the toolbar 415) to create the waypoint 305. The view corresponding to the created waypoint 305 may or may not be captured and stored.

In some examples, in addition to or alternative to creation of a single or multiple independent waypoints 305 as described above, a series of one or more waypoints 305 may be created automatically during the operation. For example, the surgeon 101 may provide input (e.g., using the toolbar 415) to start creation of a series of waypoints 305, for example at a specified time or distance interval (which may be predefined during pre-operative planning, for example). The surgeon 101 may specify the time and/or position at which waypoint creation should begin (e.g., by providing intraoperative input, such as depression of a foot pedal, indicating start of waypoint creation, or by predefining a start time and/or position during pre-operative planning) and may further specify the time and/or position at which waypoint creation should end (e.g., by providing intraoperative input, such as release of a foot pedal, or by predefining an end time and/or position during pre-operative planning).

Figure 5:
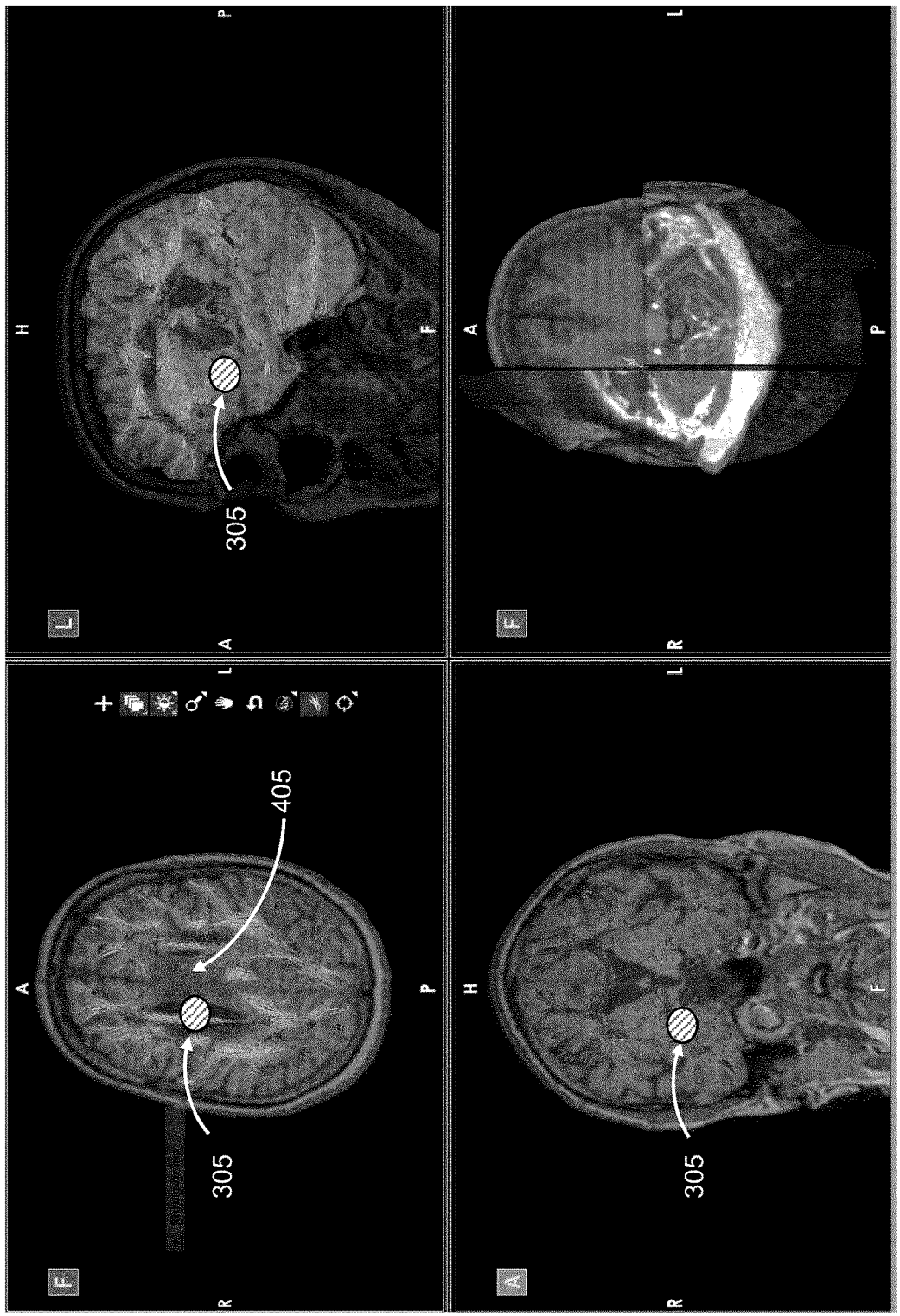
FIG. 5 shows another example user interface for providing navigational feedback, in which three cross-sectional views are shown.

FIG. 5 shows another example user interface that may be displayed intraoperatively to provide navigational feedback. The user interface of FIG. 5 may be provided in addition to or in place of the user interface shown in FIG. 4, for example. In the example user interface of FIG. 5, superior, posterior and lateral cross-sectional views of the 3D image 405 are displayed in the upper-left, lower-left and upper-right portions, respectively, of the user interface. The waypoint 305 is displayed in its corresponding location in each of the cross-sectional views. The lower-right portion of the user interface shows the 3D image 405, with lines and cutaways representing the location of the three cross-sectional views. The cross-sectional views are along Cartesian planes corresponding to the position and orientation of the waypoint 305.

The user interface shown in FIG. 5 shows images of the surgical field, including indication of the waypoint 305 but without indication of the access port 210 or other surgical tool. The user interface of FIG. 5 may be the result of retrieving previously captured views associated with the intraoperatively created waypoint 305, for example, or may be the result of the access port 210 having been removed from the surgical field. When the access port 210 is reintroduced to the surgical field, the surgeon 101 may use the indication of the waypoint 305 in the different views to guide the access port 210 back to the stored position and orientation.

Figure 6:
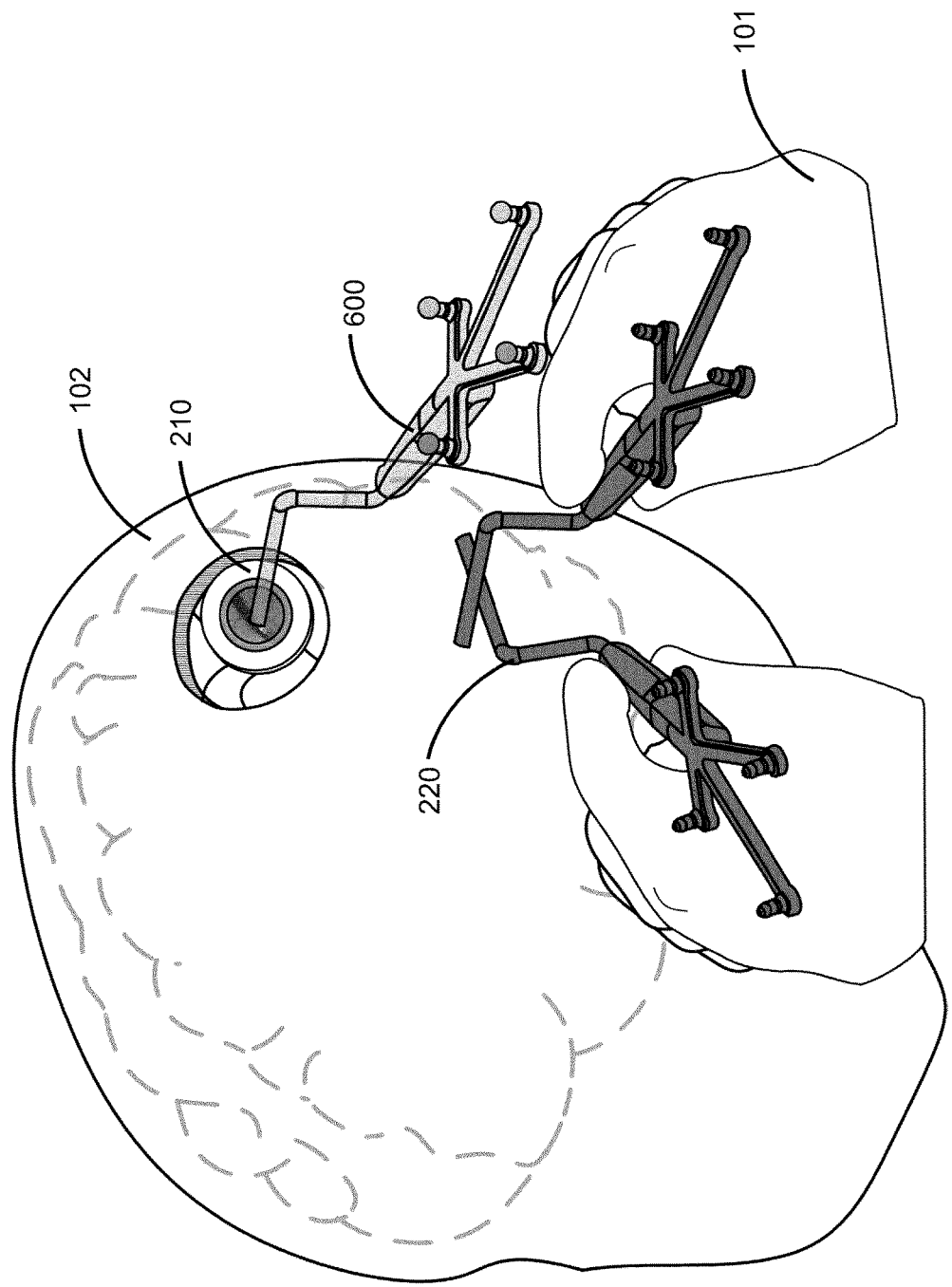
FIG. 6 shows an example of a user interface that may be provided as an augmented reality display, in which an indicator of a waypoint is shown as a ghost representation of a surgical tool.

FIG. 6 shows an example of a user interface, also referred to as an augmented reality display, which may be provided via augmented reality glasses 310 worn by the surgeon 101 during the surgical procedure. The augmented reality glasses 310 may be coupled to or otherwise communicate with the navigation system 200 (e.g., wirelessly) to enable the augmented reality glasses 310 to display navigational information (e.g., indicator(s) of waypoint(s) and/or information about position and orientation of the tracked surgical tool 220) in the augmented reality display. In some examples, the navigation system 200 generates the augmented reality display to be displayed by the augmented reality glasses 310. In other examples, the navigation system 200 may provide information to another system, for example an exoscope, that generates the augmented reality display.

In this example, the actual patient 102, surgeon 101, access port 210 and surgical tools 220 are viewable in the augmented reality display. Optionally, a virtual outline of the patient's brain may be displayed. The augmented reality display shows a virtual depiction, or a ghost representation 600, of the surgical tool 220 superimposed on the surgical field. The ghost representation 600 corresponds to the position and orientation of the surgical tool 220 corresponding to the stored position and orientation of an intraoperatively created waypoint.

The ghost representation 600 may realistically correspond to the size, shape and appearance of the surgical tool 220, but may be displayed as a shadow or faint image. Such feedback may help the surgeon 101 to more easily manoeuvre the tool 220 to the appropriate position and orientation to return to the stored waypoint, simply by matching the actual tool 220 to the depicted ghost representation 600.

Figure 7:
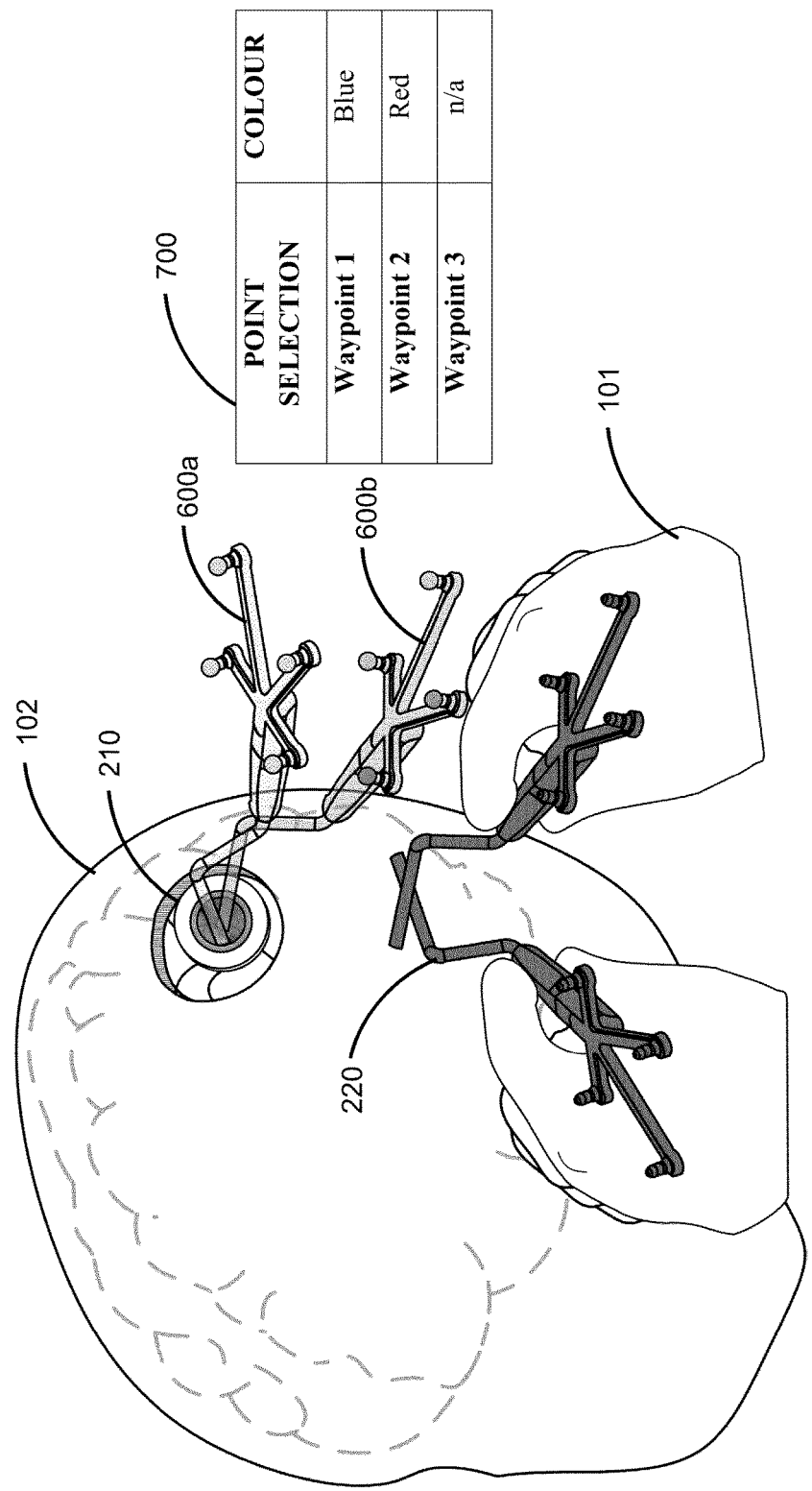
FIG. 7 shows an example user interface provided as an augmented reality display, in which a plurality of waypoints are indicated.

FIG. 7 shows an example user interface that may be a variant of the user interface shown in FIG. 6. In the example of FIG. 7, two waypoints may have been created intraoperatively. Accordingly, two ghost representations 600a, 600b may be shown in the augmented reality display, each ghost representation 600a, 600b corresponding to the stored position and orientation of a respective waypoint. Each ghost representation 600a, 600b may be visually different (e.g., displayed using different colours) to enable the surgeon 101 to distinguish between the two. A chart 700 may be displayed to indicate which ghost representation 600a, 600b corresponds to which waypoint.

In this example, the chart 700 indicates that the blue ghost representation 600a corresponds to waypoint 1 while the red ghost representation 600b corresponds to waypoint 2. Since a third waypoint has not been created, there is no corresponding ghost representation indicated in the chart 700. In some examples, the listed waypoints may be selectable, to enable the surgeon 101 to choose which waypoint to be represented in the augmented reality display. When a single waypoint has been selected to be represented, the user interface may become similar to that shown in FIG. 6. The chart 700 may be hidden and may be called up again in response to input from the surgeon 101, for example. Although the example chart 700 identifies the waypoints simply by number, in some examples the surgeon 101 may be provided an option to assign a label or name for each intraoperatively created waypoint (e.g., at the time that the waypoint is first created), to assist in identifying the waypoint.

Figure 8:
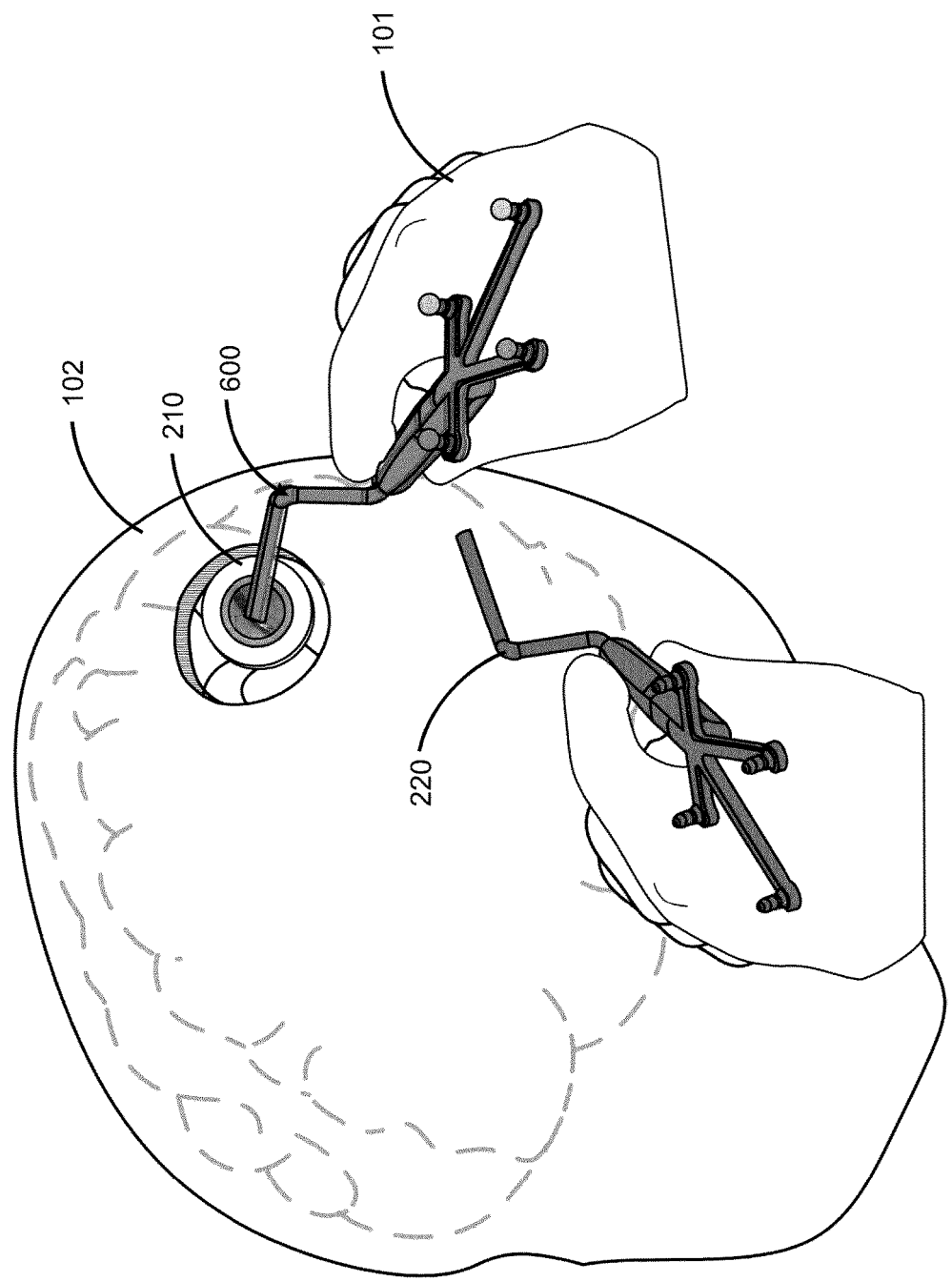
FIG. 8 shows an example user interface in which a surgical tool is aligned or nearly aligned with a waypoint.

FIG. 8 shows an example user interface in which the surgical tool 220 is aligned or nearly aligned with the stored position and orientation of the waypoint. The user interface of FIG. 6 may progress to that of FIG. 8, for example, when the surgeon 101 moves the surgical tool 220 to match the ghost representation 600. In the example of FIG. 8, when the position and orientation of the surgical tool 220 is substantially at the stored position and orientation of the waypoint (e.g., within a predefined margin of error, for example within +/−1 mm and +/−1°), feedback may be provided to indicate that the surgical tool 220 has successfully returned to the waypoint. Such feedback may include visual feedback (e.g., a change in colour of the ghost representation, or a flashing of the ghost representation), audio feedback (e.g., an audio chime, and/or a verbal cue), tactile feedback (e.g., a vibration of the augmented reality glasses and/or via the surgical tool 220, such as during a training or simulation session) and/or other suitable feedback.

After the surgical tool 220 has successfully returned to the waypoint, depiction of the waypoint may be removed from the user interface, so as to unclutter the surgeon's view. Alternatively, the depiction of the waypoint may be maintained (e.g., until manually dismissed or deleted). Even if the depiction of the waypoint is removed from the user interface, the waypoint and its stored position and orientation remain stored in memory (e.g., until manually deleted), and may be recalled to the user interface at a later time, for example.

Figure 9:
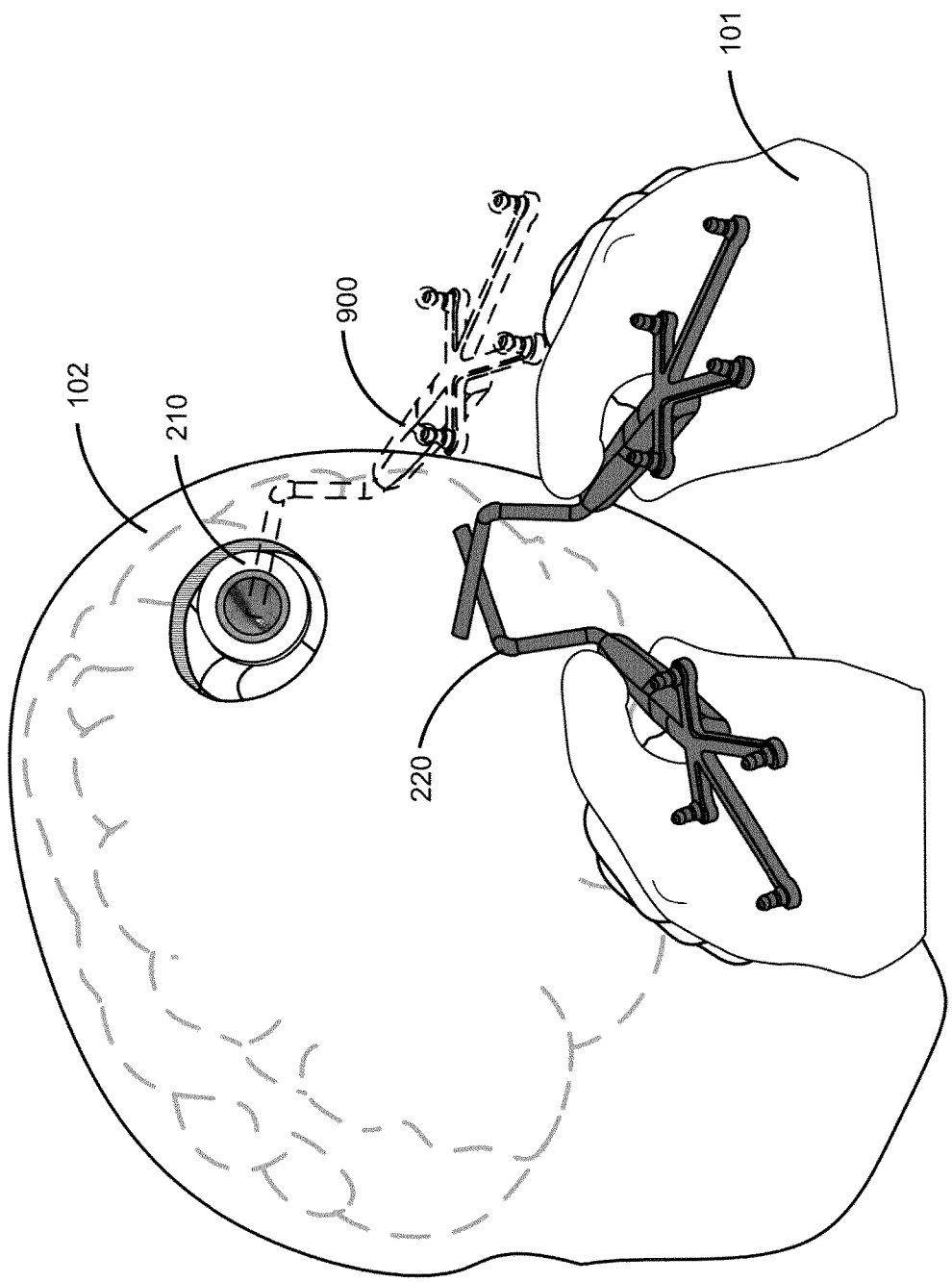
FIG. 9 shows an example user interface provided as an augmented reality display, in which an indicator of a waypoint is shown as an outline of a surgical tool.

FIG. 9 shows another example user interface, which may be similar to the user interface of FIG. 6. The example of FIG. 9 may differ from that of FIG. 6 in that instead of providing a ghost representation 600, the user interface instead provides an outline 900 representing the position and orientation that the surgical tool 220 should return to in order to return to the waypoint. FIG. 9 may be modified to show outlines 900 corresponding to more than one waypoint, for example similarly to the example of FIG. 7.

Figure 10:
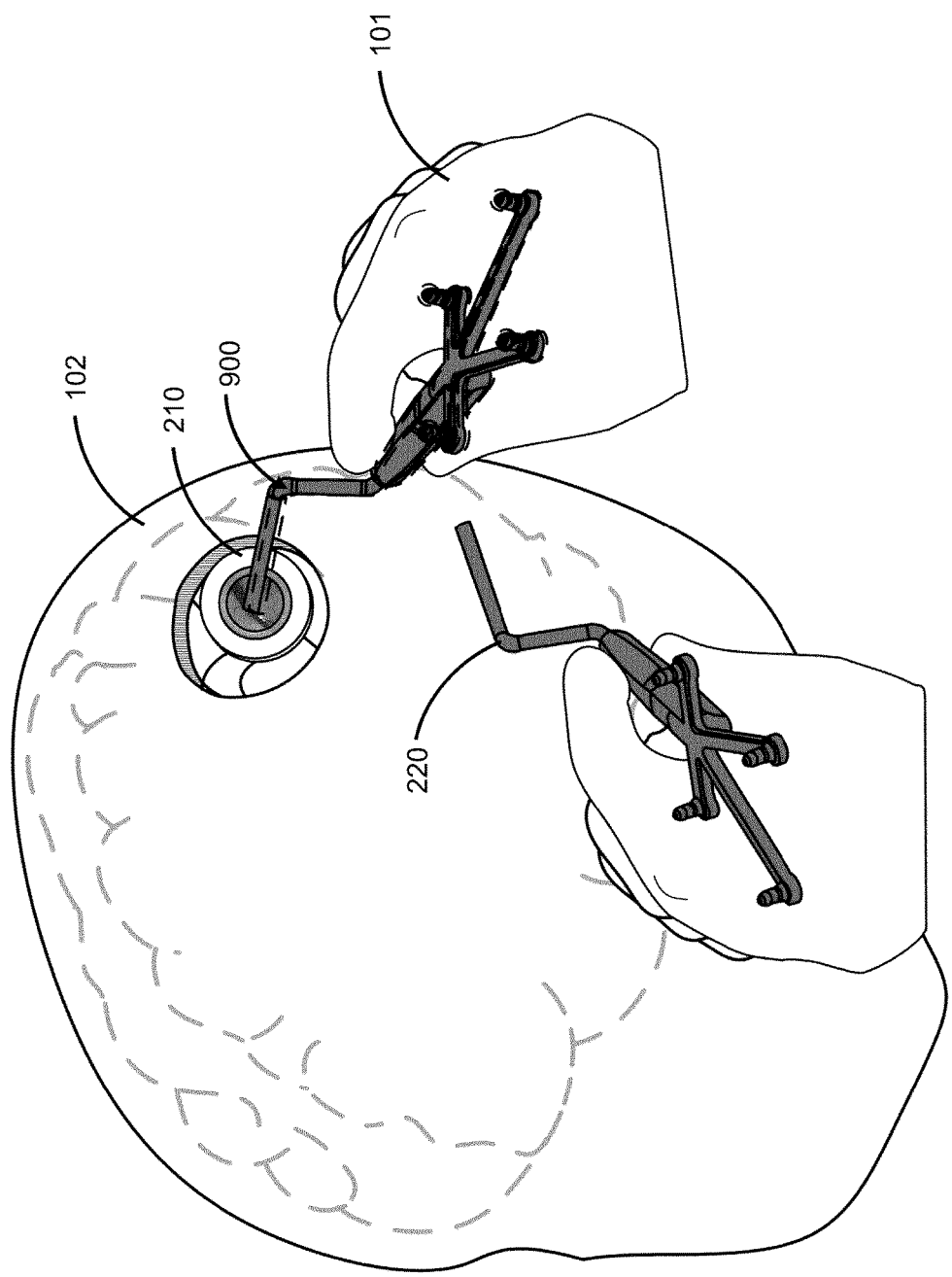
FIG. 10 shows an example user interface in which a surgical tool is aligned or nearly aligned with a waypoint.

FIG. 10 shows an example user interface in which the surgical tool 220 is completely or nearly aligned with the stored position and orientation of the waypoint. The user interface of FIG. 9 may progress to that of FIG. 10, for example, when the surgeon 101 moves the surgical tool 220 to match the outline 900. The user interface of FIG. 10 may be similar to that of FIG. 8, for example.

Figure 11:
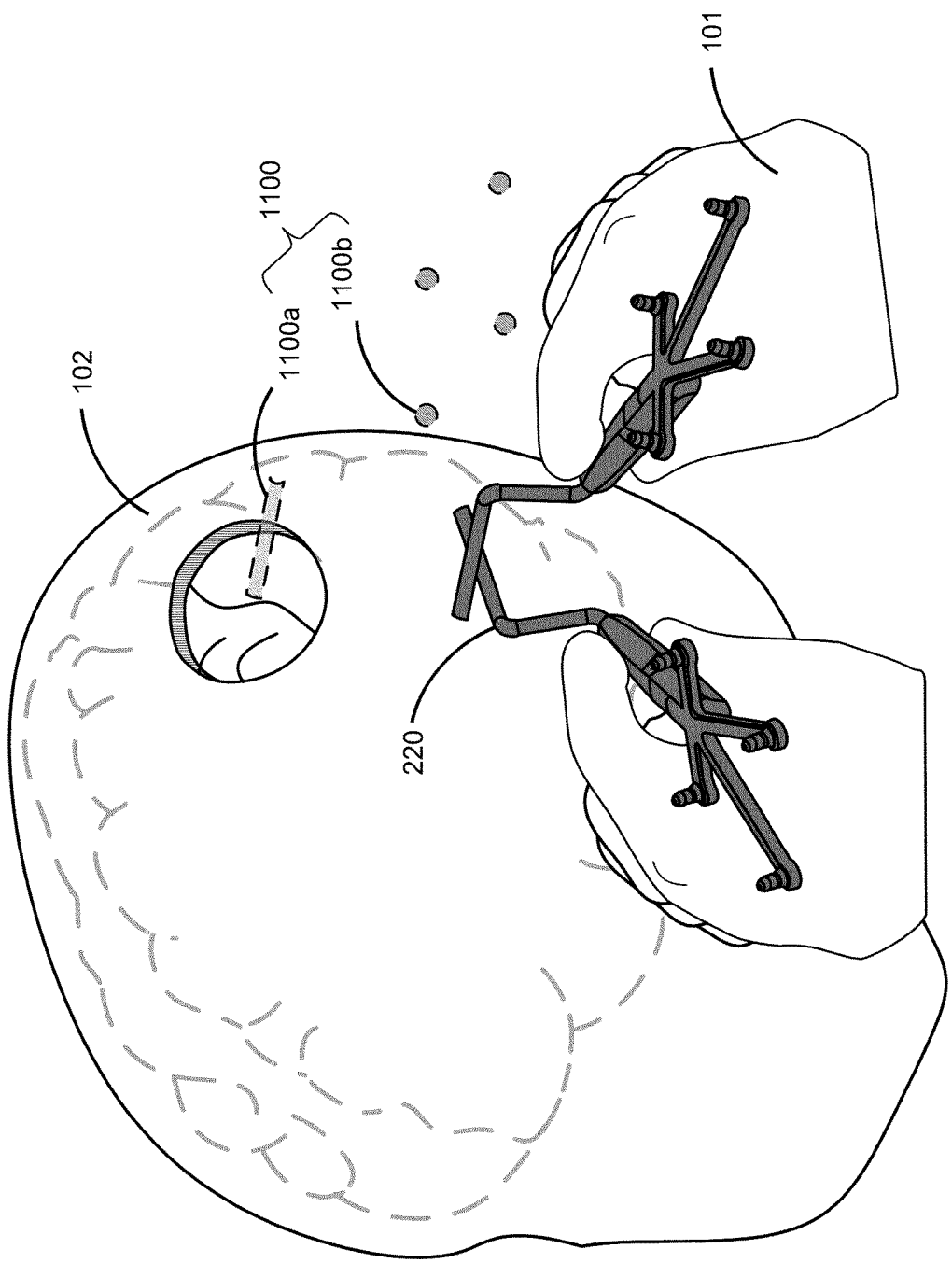
FIG. 11 shows an example user interface provided as an augmented reality display, in which an indicator of a waypoint is shown as portions of a surgical tool.

FIG. 11 shows another example user interface, which may be similar to the user interfaces of FIGS. 6 and 9. The example of FIG. 11 may differ from that of FIGS. 6 and 9 in that instead of providing a ghost representation 600 or an outline 900, the user interface instead displays a representation 1100 of only one or more portions of the surgical tool 220 (e.g., only the distal tip 1100*a* and markers 1100*b*) corresponding to the stored position and orientation of the waypoint. Further, FIG. 11 illustrates an example user interface in the context of open surgery, without use of an access port 210. FIG. 11 may be modified to show representations 1100 corresponding to more than one waypoint, for example similarly to the example of FIG. 7.

Figure 12:
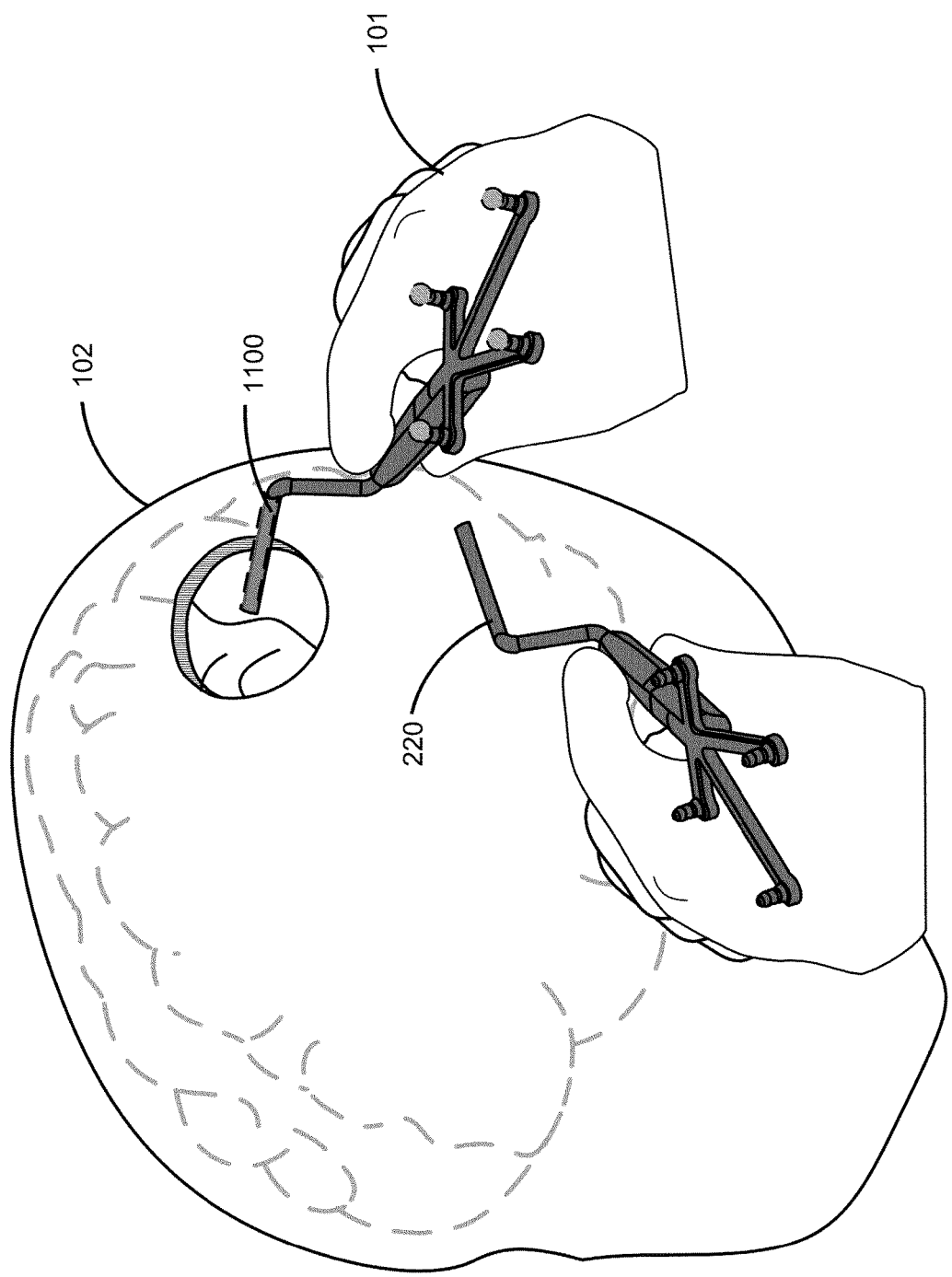
FIG. 12 shows an example user interface in which a surgical tool is aligned or nearly aligned with a waypoint.

FIG. 12 shows an example user interface in which the surgical tool 220 is completely or nearly aligned with the stored position and orientation of the waypoint. FIG. 12 illustrates an example user interface in the context of open surgery, without use of an access port 210. The user interface of FIG. 11 may progress to that of FIG. 12, for example, when the surgeon 101 moves the surgical tool 220 to match the representation 1100. The user interface of FIG. 12 may be similar to that of FIGS. 8 and 10, for example.

Although FIGS. 6-12 illustrate examples in which the user interface provides feedback indicating the position and orientation of the waypoint, for example using a representation of the surgical tool, in other examples the feedback may indicate only the position of the waypoint, for example using a simple marker (e.g., a circle). A simple marker may also provide information about both the position and orientation of the waypoint, for example using a simple 3D arrow marker. Using a simple marker rather than a representation of the surgical tool may help to reduce clutter in the user interface, may enable multiple waypoints to be more clearly displayed, and/or may enable a waypoint to be more effectively used as a reference point or landmark.

Figure 13:
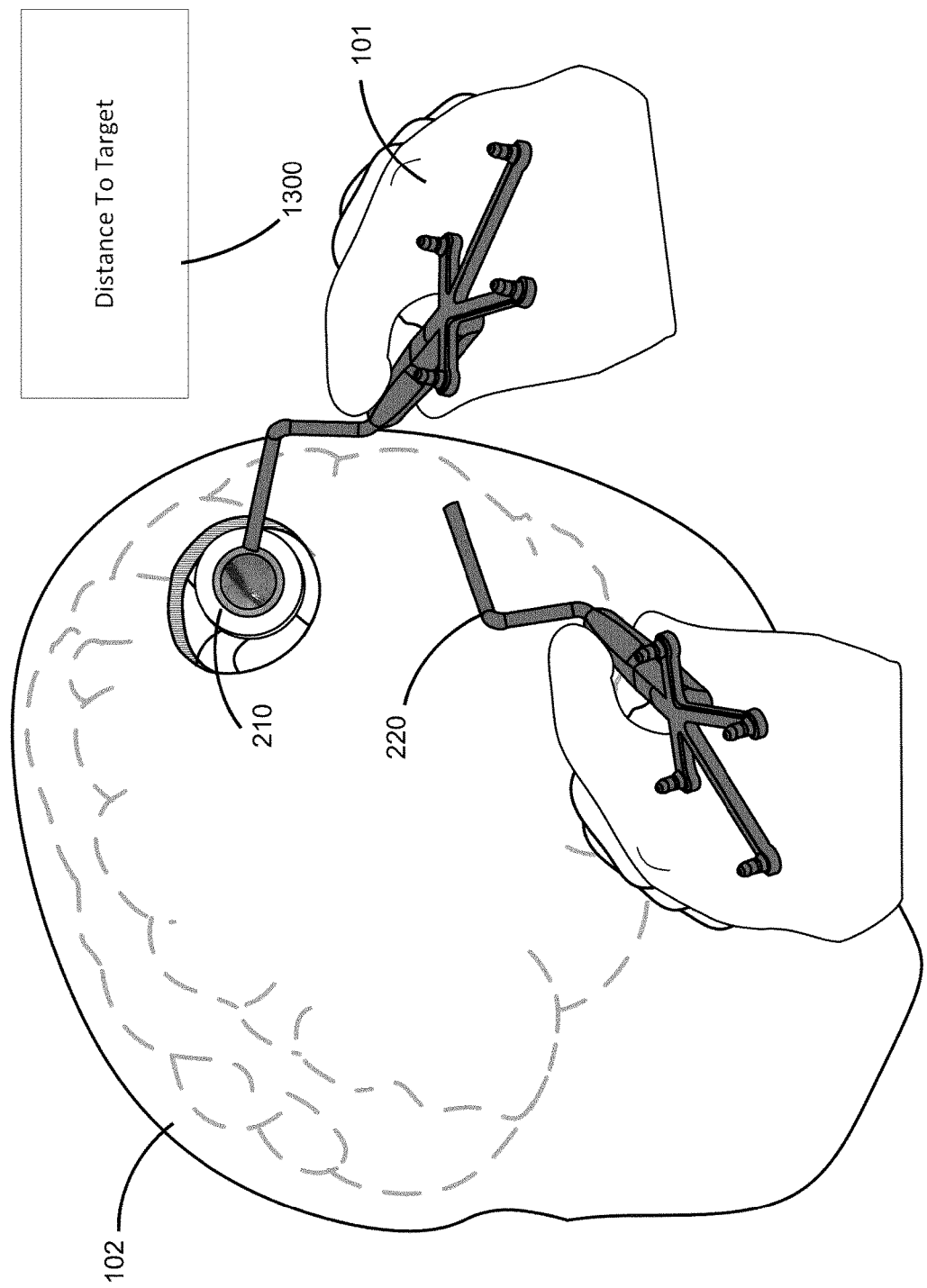
FIG. 13 shows an example user interface provided as an augmented reality display, in which navigational feedback is provided as an inset on the display.

FIG. 13 shows an example user interface in which navigational feedback is provided as textual display. In this example, instead of showing a depiction or representation of the waypoint, an inset 1300 is shown in the augmented reality display providing feedback information indicating the position and orientation of the waypoint. In the example shown, the inset 1300 displays textual indication of the distance (e.g., in Cartesian coordinates) between the currently position of the surgical tool 220 (e.g., as tracked by the navigation system 200) and the stored position and orientation of the waypoint. In some examples, the inset 1300 may also provide information to guide return of the surgical tool 220 to the waypoint 305, for example information about the direction in which the surgical tool 220 should be moved and/or how the surgical tool 220 should be rotated (e.g., in pitch, yaw and roll) to return to the waypoint.

In some examples, the inset 1300 may be provided in a display of cross-sectional views (e.g., as in FIGS. 4 and 5). In some examples, the inset 1300 may be provided in addition to a visual representation of the waypoint, such as the representations shown in FIGS. 4-12. Where there are multiple waypoints, the inset 1300 may provide information for all the waypoints, may highlight information for a particular selected waypoint, or may provide information only for one selected waypoint.

The user interface may provide selectable options for switching among various available feedback modes.

Figure 14:
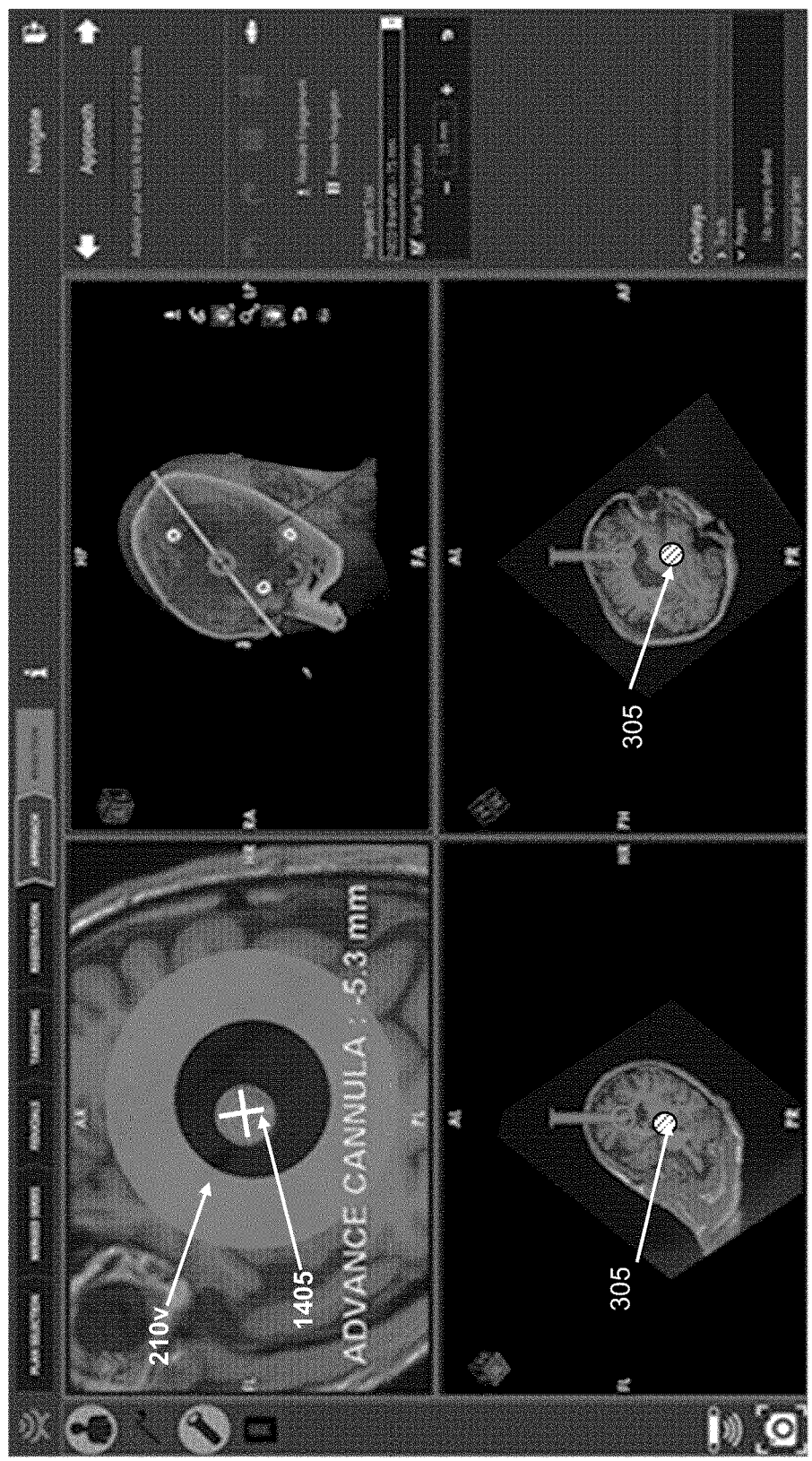
FIG. 14 shows an example user interface in which an intraoperatively created waypoint is presented during navigation of an access port.

FIG. 14 shows an example user interface in which an intraoperatively created waypoint may be presented in the user interface during navigation of an access port. The user interface of FIG. 14 may include elements similar to those of FIG. 4, for example including multiple cross-sectional views of the surgical field (in this example, a patient's brain), and a virtual representation 210*v* of the access port (in this example, an access cannula) corresponding to the actual position and location of the access port in the surgical field.

In this example, the waypoint 305 may be presented in a format that may be familiar to the surgeon, for example similarly to presentation of a pre-operatively defined navigational target (e.g., a pre-operatively defined tumour). The user interface may provide one or more visual aids to help guide navigation of the surgical tool to the position and orientation of a waypoint. For example, the user interface may include a set of targets 1405 (e.g., a set of double cross hairs that align along an axis matching the orientation of the waypoint) for the surgeon to align the axis of the surgical tool, to match the orientation of the waypoint, and further indicators for the surgeon to advance the surgical tool, until the position of the waypoint has been reached. In some examples, the user interface may display a cone to help the surgeon to align the axis of the surgical tool, to match the orientation of the waypoint. In some examples, the user interface may present the surgical field as a view where the viewing plane is orthogonal to the axis of the surgical tool (e.g., a predefined axis of the surgical tool, which may be predefined by default) and the center of the viewing plane is located on the axis line. In addition, an indicator (e.g., a crosshair) may be provided at the center of the viewing plan to indicate the projected position of the surgical tool (i.e., where the axis line intersects the viewing plane) on the user interface view. As shown in the example of FIG. 14, the user interface may also provide textual information, for example to indicate the distance and/or direction the surgical tool (e.g., a cannula) should be moved in order to match a waypoint.

FIGS. 4-14 show a number of examples of how an indicator of the stored position and orientation of the waypoint may be displayed in a user interface. Other representations and indicators may be used, for example cursors, symbols, and other 2D and/or 3D depictions.

In some examples, a waypoint may provide further information to guide the surgical procedure. For example, a waypoint may include an indicator (e.g., an icon or label) indicating the direction and/or location of a region of interest (ROI) (e.g., a lesion) relative to the waypoint. This may be useful to help a surgeon to navigate to the ROI. The indicator provided by the waypoint may be generated automatically (e.g., by the system automatically determining the location and/or direction of a predefined ROI relative to the waypoint, for example when the waypoint is first created) and/or may be added by the surgeon (e.g., using the user interface).

In some examples, information about the stored waypoint(s) may be toggled on and off during the procedure. For example, a surgeon may deselect a no longer needed waypoint to remove depiction of the waypoint from the user interface, to avoid visual clutter. A deselected waypoint may still be maintained in memory, such that it may be displayed again if later selected by the surgeon; further deletion input may be required to delete the waypoint from memory. Alternatively, deselection of a waypoint may result in the waypoint being automatically deleted from memory.

In some examples, the surgeon may be provided options for modifying an intraoperatively created waypoint. For example, after a waypoint has been created and stored in memory, the surgeon may be able to adjust the orientation and/or position of the waypoint using software commands (e.g., click-and-drag commands using a mouse), without having to create a new waypoint. The modified waypoint may be stored in memory in place of or in addition to the originally created waypoint.

In some examples, a record of all waypoints created during the procedure may be generated. A waypoint may be identified in the record by its orientation and position (e.g., in x, y, z, pitch, yaw and roll coordinates) relative to a reference point. The record may be generated in real-time, as each waypoint is created, or may be generated at a certain time-point (e.g., at the end of the procedure and/or in response to user input). The record may include all waypoints created, including those that were deleted and/or modified. The record may be stored together with other information about the procedure. The record may be useful for quality assurance and/or training purposes, for example.

For example, in a training situation, a virtual or phantom model of the patient may be provided to a trainee together with the stored record of previously created waypoints. The trainee may then practice (e.g., in virtual space or on the phantom model) navigating a surgical tool to the waypoints. During this training, audio and/or tactile feedback may be provided (e.g., as described above) to help the trainee learn and improve in navigation skills. In another example, in a training or quality assurance situation, the record of waypoints created during a procedure may be reviewed by a more senior surgeon, to ensure that navigation of the surgical tool was appropriate to the surgical procedure.

Figure 15:
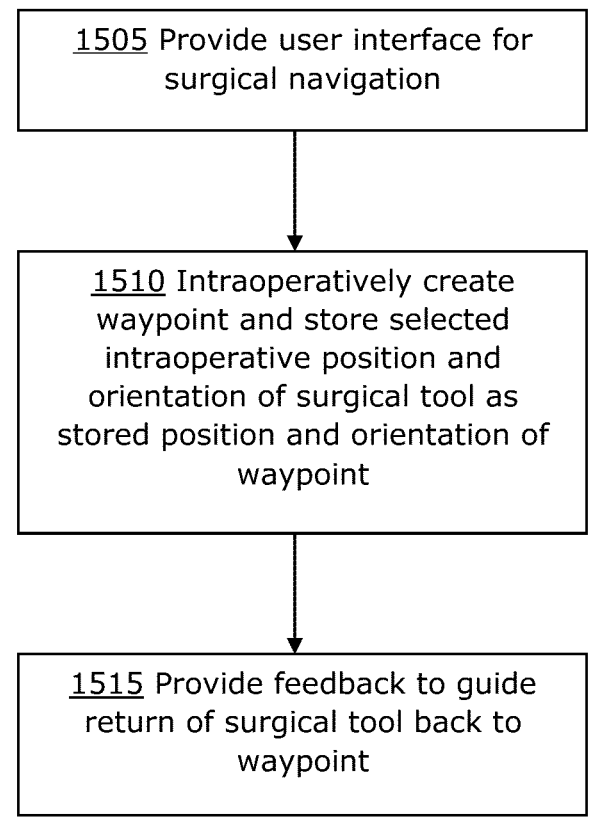
FIG. 15 is a block diagram of an example system configuration, including a control and processing unit and external components.

FIG. 15 shows a flowchart illustrating an example method 1500 for providing navigational feedback during a surgical procedure. The method 1500 may be implemented using any of the example user interfaces discussed above, for example.

At 1505, a user interface is provided (e.g., via a display 205, 211 of the navigation system 200 and/or via an augmented reality device) for surgical navigation. The user interface may enable viewing of the position and orientation of the surgical tool 220 in the surgical field during the surgical procedure. The position and orientation of the surgical tool may be tracked by the navigation system 200, for example, and this tracking information may be presented to the user via the user interface (e.g., as a virtual representation of the surgical tool superimposed on an image of the surgical field).

At 1510, a waypoint is created intraoperatively by selecting a position and orientation of the surgical tool 220 (e.g., typically the current position and orientation of the surgical tool) and storing this position and orientation in a memory as the waypoint.

At 1515, after the surgical tool 220 has been moved from the selected position and orientation, the user may be provided with feedback (e.g., visual, audio, tactile and/or other forms of feedback) to indicate the position and/or orientation of the waypoint. This feedback may be provided using any of the example user interfaces discussed herein, for example. In some examples, the feedback may include the captured view associated with the stored position and orientation of the waypoint, thus enabling the user to view the view(s) associated with the waypoint without requiring the surgical tool 220 to return to the position and orientation of the waypoint.

Although the above discussion provides examples in which navigational feedback is provided visually to indicate the position and/or orientation of the waypoint, it should be understood that in some examples other types of feedback may be provided in addition to or in place of visual feedback. For example, audio and/or tactile feedback may be provided in addition to or in place of visual feedback. Audio feedback may include chimes or beeps that may increase/decrease in pitch/frequency as the surgical tool gets nearer to or farther from the position and orientation of the waypoint, and/or may include verbal cues indicating the distance between the surgical tool and the waypoint, for example. Tactile feedback may include vibrations and/or beats that may be felt through equipment in contact with the surgeon (e.g., via the augmented reality glasses and/or via the surgical tool).

Although the above discussion refers to the surgeon as being the user who controls and uses the examples of the present disclosure, it should be understood that the present disclosure is not limited to any specific user. In some examples, there may be a plurality of users involved. For example, a surgical assistant, such as a nurse or operator, may be involved in creation of the waypoint and the augmented reality display may be provided to the surgeon.

While some embodiments or aspects of the present disclosure may be implemented in fully functioning computers and computer systems, other embodiments or aspects may be capable of being distributed as a computing product in a variety of forms and may be capable of being applied regardless of the particular type of machine or computer readable media used to actually effect the distribution.

At least some aspects disclosed may be embodied, at least in part, in software. That is, some disclosed techniques and methods may be carried out in a computer system or other data processing system in response to its processor, such as a microprocessor, executing sequences of instructions contained in a memory, such as ROM, volatile RAM, non-volatile memory, cache or a remote storage device.

A computer readable storage medium may be used to store software and data which when executed by a data processing system causes the system to perform various methods or techniques of the present disclosure. The executable software and data may be stored in various places including for example ROM, volatile RAM, non-volatile memory and/or cache. Portions of this software and/or data may be stored in any one of these storage devices.

Examples of computer-readable storage media may include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Furthermore, at least some of the methods described herein may be capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

At least some of the elements of the systems described herein may be implemented by software, or a combination of software and hardware. Elements of the system that are implemented via software may be written in a high-level procedural language such as object oriented programming or a scripting language. Accordingly, the program code may be written in C, C++, J++, or any other suitable programming language and may comprise modules or classes, as is known to those skilled in object oriented programming. At least some of the elements of the system that are implemented via software may be written in assembly language, machine language or firmware as needed. In either case, the program code can be stored on storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

While the teachings described herein are in conjunction with various embodiments for illustrative purposes, it is not intended that the teachings be limited to such embodiments. On the contrary, the teachings described and illustrated herein encompass various alternatives, modifications, and equivalents, without departing from the described embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

The invention claimed is:

1. A method of providing navigational feedback during a surgical procedure by way of a processor, the method comprising:
    providing an augmented reality display, displayed on an augmented reality display device coupled with the processor, for viewing a three-dimensional (3D) position and an orientation of a surgical tool in a surgical field during the surgical procedure, the position and the orientation of the surgical tool being tracked by a medical navigation system coupled with the processor, and the augmented reality display comprising a virtual representation of the surgical tool superimposed on a live, real-time image of the surgical field;
    automatically intraoperatively creating a waypoint and storing, in a memory coupled to the processor, a selected intraoperative start time, a selected intraoperative end time, a selected intraoperative 3D position, and a selected intraoperative orientation of the surgical tool as a stored start time, a stored end time, a stored position, and a stored orientation of the waypoint, the stored position comprising x, y, and z coordinates, and the stored orientation comprising pitch, yaw, and roll;
    providing feedback to indicate the stored start time, the stored end time, the stored position, and the stored orientation of the waypoint, the feedback comprising information to guide return of the surgical tool to the waypoint after the surgical tool has been moved from the selected intraoperative position and the selected intraoperative orientation; and
    when the surgical tool has returned to the stored position and the stored orientation of the waypoint prior to the stored end time, providing further feedback indicating a successful return of the surgical tool to the waypoint.

2. The method of claim 1, wherein providing the feedback comprises providing information indicating at least one of a direction, a location, and a distance of at least one region of interest relative to the waypoint.

3. The method of claim 1, wherein providing the feedback comprises displaying the feedback on the augmented reality display.

4. The method of claim 3, wherein the providing the feedback comprises displaying the feedback as superimposed on the image of the surgical field.

5. The method of claim 3, wherein displaying the feedback comprises displaying a ghost representation of the surgical tool corresponding to the stored position and the stored orientation of the waypoint as superimposed on the image of the surgical field.

6. The method of claim 3, wherein displaying the feedback comprises displaying an indicator of at least one of a position, a distance, and a direction of the stored position and the stored orientation of the waypoint relative to a current position of the surgical tool as superimposed on the image of the surgical field.

7. The method of claim 3, wherein displaying the feedback comprises displaying a visual aid to guide navigation of the surgical tool to the stored position and the stored orientation of the waypoint as superimposed on the image of the surgical field.

8. The method of claim 7, wherein displaying the visual aid comprises displaying a set of targets, indicating the stored position of the waypoint and indicating an axis to which the surgical tool should align, to match the stored orientation of the waypoint.

9. The method of claim 7, wherein displaying the visual aid comprises displaying a cone to guide alignment of the surgical tool to match the stored orientation of the waypoint.

10. The method of claim 3, wherein displaying the feedback comprises displaying an indicator of the stored position and the stored orientation of the waypoint as superimposed on the image of the surgical field.

11. The method of claim 1, wherein providing the feedback comprises providing at least one of audio feedback and tactile feedback to indicate the stored position and the stored orientation of the waypoint.

12. The method of claim 1 further comprising: intraoperatively, in response to a deselection input, removing display of the feedback.

13. The method of claim 12 further comprising: in response to the deselection input, deleting the stored position and the stored orientation of the waypoint from the memory.

14. The method of claim 1 further comprising:
intraoperatively, in response to a modification input, modifying at least one of the stored position the stored orientation of the waypoint; and
updating the feedback to correspond to at least one of a modified position a modified orientation of the waypoint.

15. The method of claim 1 further comprising:
creating a record of all intraoperatively created waypoints during the surgical procedure; and
transmitting an output of the record.

16. The method of claim 1, wherein automatically intraoperatively creating the waypoint comprises automatically intraoperatively creating a series of one or more waypoints at a predefined interval.

17. The method of claim 1,
wherein the waypoint is configured to be displayed in multiple views,
wherein providing the feedback comprises providing visual feedback, audio feedback, and tactile feedback,
wherein providing the visual feedback comprises providing at least one of a textual display having information regarding a direction in which the surgical tool should at least one of move and rotate to return to the waypoint, a color change, and a flash,
wherein providing the audio feedback comprises providing at least one of a chime, a cue, and a beep,
wherein providing the audio feedback comprises providing the audio feedback with at least one of a variable pitch and a variable frequency as a function distance between the surgical tool and the waypoint, and
wherein providing the tactile feedback comprises providing a vibration of the augmented reality display device.

18. A system for providing navigational feedback during a surgical procedure, the system comprising:
an augmented reality display device for displaying an augmented reality display, the augmented reality display comprising a display of a virtual representation of a tracked three-dimensional (3D) position and an orientation of a surgical tool superimposed on a live, real-time image of a surgical field, the position and the orientation of the surgical tool being tracked by a medical navigation system during the surgical procedure; and
a processor coupled to the medical navigation system and the augmented reality display device, the processor being configured to execute a set of instructions to:
automatically intraoperatively create a waypoint and storing, in a memory coupled with the processor, a selected intraoperative start time, a selected intraoperative end time, a selected intraoperative 3D position, and a selected intraoperative orientation of the surgical tool as a stored start time, a stored end time, a stored position, and a stored orientation of the waypoint, the stored position comprising x, y, and z coordinates, and the stored orientation comprising pitch, yaw, and roll;
provide feedback to indicate the stored start time, the stored end time, the stored position, and the stored orientation of the waypoint, the feedback comprising information to guide return of the surgical tool to the waypoint after the surgical tool has been moved from the selected intraoperative position and the selected intraoperative orientation; and
when the surgical tool has returned to the stored position and the stored orientation of the waypoint prior to the stored end time, providing further feedback indicating a successful return of the surgical tool to the waypoint.

19. The system of claim 18 further comprising: the medical navigation system configured to track the 3D position and orientation of the surgical tool in the surgical field during the surgical procedure.

20. The system of claim 18,
wherein the waypoint is configured to be displayed in multiple views,
wherein the feedback comprises visual feedback, audio feedback, and tactile feedback,
wherein the visual feedback comprises at least one of a textual display having information regarding a direction in which the surgical tool should at least one of move and rotate to return to the waypoint, a color change, and a flash,
wherein the audio feedback comprises at least one of a chime, a cue, and a beep, and
wherein the tactile feedback comprises a vibration of the augmented reality display device.

21. A computer readable product for providing navigational feedback during a surgical procedure, the computer readable product comprising a set of computer-executable instructions that, when executed, causes a computer system to:
provide an augmented reality display, displayed on an augmented reality display device coupled to the processor, for viewing a three-dimensional (3D) position and an orientation of a surgical tool in a surgical field during the surgical procedure, the position and the orientation of the surgical tool being tracked by a medical navigation system coupled to the processor, the augmented reality display comprising a virtual representation of the surgical tool superimposed on a live, real-time image of the surgical field;
automatically intraoperatively create a waypoint and storing, in a memory coupled with the processor, a selected intraoperative start time, a selected intraoperative end time, a selected intraoperative 3D position, and a selected intraoperative orientation of the surgical tool as a stored start time, a stored end time, a stored position, and a stored orientation of the waypoint, the stored position comprising x, y, and z coordinates, and the stored orientation comprising pitch, yaw, and roll;
provide feedback to indicate the stored start time, the stored end time, the stored position and the stored orientation of the waypoint, the feedback comprising information to guide return of the surgical tool to the waypoint after the surgical tool has been moved from the selected intraoperative position and the selected intraoperative orientation; and
when the surgical tool has returned to the stored position and the stored orientation of the waypoint prior to the stored end time, providing further feedback indicating a successful return of the surgical tool to the waypoint.

22. The computer-readable product of claim 21,
wherein the waypoint is configured to be displayed in multiple views, wherein the feedback comprises visual feedback, audio feedback, and tactile feedback,
wherein the visual feedback comprises at least one of a textual display having information regarding a direction in which the surgical tool should at least one of move and rotate to return to the waypoint, a color change, and a flash,
wherein the audio feedback comprises at least one of a chime, a cue, and a beep, and
wherein the tactile feedback comprises a vibration of the augmented reality display device.

* * * * *